United States Patent
Damment et al.

(10) Patent No.: US 11,324,746 B2
(45) Date of Patent: May 10, 2022

(54) USE OF ANAGRELIDE FOR TREATING CANCER

(71) Applicant: Arovella Therapeutics Limited, Osborne Park (AU)

(72) Inventors: Stephen Damment, Southampton (GB); Richard Franklin, Southampton (GB); Jorge D. Erusalimsky, Cardiff (GB)

(73) Assignee: AROVELLA THERAPEUTICS LIMITED, Osborne Park (AU)

( * ) Notice: Subject to any disclaimer, the term of this patent is extended or adjusted under 35 U.S.C. 154(b) by 0 days.

(21) Appl. No.: 15/538,326

(22) PCT Filed: Dec. 22, 2015

(86) PCT No.: PCT/GB2015/054116
§ 371 (c)(1),
(2) Date: Jun. 21, 2017

(87) PCT Pub. No.: WO2016/102952
PCT Pub. Date: Jun. 30, 2016

(65) Prior Publication Data
US 2017/0360793 A1      Dec. 21, 2017

(30) Foreign Application Priority Data
Dec. 22, 2014   (GB) .................................... 1422978

(51) Int. Cl.
*A23K 50/10*    (2016.01)
*A23K 20/158*   (2016.01)
*A61K 31/519*   (2006.01)
*A61K 47/26*    (2006.01)

(52) U.S. Cl.
CPC ............ *A61K 31/519* (2013.01); *A61K 47/26* (2013.01); *A61L 2300/42* (2013.01)

(58) Field of Classification Search
None
See application file for complete search history.

(56) References Cited

U.S. PATENT DOCUMENTS

| | | | | |
|---|---|---|---|---|
| 2010/0111901 | A1* | 5/2010 | Gant | ................. A61K 31/4196 424/85.2 |
| 2014/0037629 | A1 | 2/2014 | Wisniewski et al. | |

FOREIGN PATENT DOCUMENTS

| | | |
|---|---|---|
| WO | WO-2004/064841 A1 | 8/2004 |
| WO | WO-2008/065445 A1 | 6/2008 |
| WO | WO-2011/117391 A2 | 9/2011 |
| WO | WO-2014/164704 A2 | 10/2014 |
| WO | WO-2014/183673 A1 | 11/2014 |
| WO | WO-2015/055898 A2 | 4/2015 |
| WO | WO-2016/062269 A1 | 4/2016 |

OTHER PUBLICATIONS

Fleming et al. ("Anagrelide." Cardiovascular Therapeutics 1.1 (1983): 277-294).*
Stravodimou et al. (Pretreatment Thrombocytosis as a Prognostic Factor in Metastatic Breast Cancer, International Journal of Breast Cancer, vol. 2013, Article ID 289563, 6 pages, 2013).*
Honn et al. (Prostacyclin: A Potent Antimetastatic Agent.Science, vol. 212, Jun. 12, 1981).*
Andes et al., "Inhibition of Platelet Production Induced by an Antiplatelet Drug, Anagrelide, in Normal Volunteers," Thromb Haemostas 52(3):325-328 (1984).
Gastpar, "Platelet-Cancer Cell Interaction in Metastasis Formation: A Possible Therapeutic Approach to Metastasis Prophylaxis," Journal of Medicine 8(2):103-114 (1977).
Hong et al., "Comparison Between Anagrelide and Hydroxycarbamids in their Activities Against Haematopoietic Progenitor Cell Growth and Differentiation: Selectivity of Anagrelide for the Megakaryoctic Lineage," Leukemia, 20:1117-1122 (2006).
Honn et al., "Prostacyclin: A Potent Antimetastatic Agent," Science, 212 1270-1272 (1981).
James, "Anagrelide-Induced Cardiomyopathy," Pharmacotherapy, 20(10):1224-1227 (2000).
Mazur et al., "Analysis of the Mechanism of Anagrelide-Induced Thrombocytopenia in Humans," Blood, 79(8):1931-1937 (1992).
Bin et al., "Mechanism of Platelet Underlying Metastasis of Malignant Tumors," J Chinese PLA Postgrad Med Sch, 32(8):871-873 (2011).
Ambrus et al., "Effect of Imidaoquinazolinones on Tumor Cells in the Circulation," J Med, 17(3-4): 219-226 (1986).
Chen et al., "Platelet-lowering Therapy with Anagrelide as an Adjuvant Therapy for Treatment of Primary Pulmonary Neoplasm-associated Extreme Thrombocytosis," Jpn J Clin Oncol, 42(8): 761-763 (2012).
Cho et al., "Platelets Increase the Proliferation of Ovarian Cancer Cells," Blood, 120(24): 4869-4872 (2012).
Gasic et al., "Antimetastatic Effects Associated with Platelet Reduction," P Natl Acad Sci USA, 61(1): 46-52 (1968).
Gay et al., "Contribution of Platelets to Tumor Metastasis," Nat Rev Cancer, 11(2): 123-134 (2011).
Hasselbalch, "The Platelet-Cancer Loop in Myeloproliferative Cancer. Is Thrombocythemia an Enhancer of Cancer Invasiveness and Metastasis in Essential Thrombocythemia, Polycythemia vera and Myelofibro," Leukemia Res, 38(10): 1230-1236 (2014).
International Search Report and Written Opinion for International Application No. PCT/GB2015/054116 dated Apr. 18, 2016.
Karpatkin et al., "Role of Adhesive Proteins in Platelet Tumor Interaction in Vitro and Metastasis Formation in Vivo," J Clin Invest, 81(4): 1012-1019 (1988).
Labelle et al., "Direct Signaling between Platelets and Cancer Cells Induces an Epithelial-Mesenchymal-Like Transition and Promotes Metastasis," Cancer Cell, 20(5): 576-590 (2011).

(Continued)

*Primary Examiner* — Layla Soroush
(74) *Attorney, Agent, or Firm* — Haug Partners LLP

(57) ABSTRACT

The present invention relates to the use of the anti-megakaryocytic agent anagrelide, or a therapeutically active metabolite thereof, in the prevention or treatment of metastatic disease in cancer patients displaying paraneoplastic thrombocytosis.

13 Claims, 4 Drawing Sheets

(56) References Cited

OTHER PUBLICATIONS

Labelle et al., "Platelets Guide the Formation of Early Metastic Niches," P Natl Acad Sci USA, 111(30): E3053-E3061 (2014).

Li et al., "Presence of Intratumoral Platelets is Associated with Tumor Vessel Structure and Metastasis," BMC Cancer, 14(1): 167 (2014).

Pearlstein et al., "Effect of Antiplatelet Antibody on the Development of Pulmonary MA Tastases Following Injection of CT26 Colon Adenocarcinoma, Lewis Lung Carcinoma, and B16 Amelanotic Melanoma Tumor Cells into Micel," Cancer Res, 44(9): 3884-3887 (1984).

Rachidi et al., "Lower Circulating Platelet Counts and Antiplatelet Therapy Independently Predict Better Outcomes in Patients with Head and Neck Squamos Cell Carcinoma," J Hematol Oncol, 7(1): 65 (2014).

Silver, "Anagrelide is Effective in Treating Patients with Hydroxyurea-resistant Thrombocytosis in Patients with Chronic Myeloid Leukemia," Leukemia, 19(1): 39-43 (2005).

Trapp et al., "Anagrelide for Treatment of Patients with Chronic Myelogenous Leukemia and a High Platelet Count," Blood Cell Mol Dis, 24(1): 9-13 (1998).

Voglova et al., "Combination of Imatinib and Anagrelide in Treatment of Chronic Myeloid Leukemia in Blastic Phase," Vnitrini Llekarstvi, 52(9): 819-822 (2006).

Agrylin® (anagrelide hydrochloride) Capsules, Rx only.

Balduini et al., "Effect of anagrelide on platelet count and function in partients with thrombocytosis and myeloproliferative disorders," Haematologica, 77:40-43 (1992).

Martinez-Selles et al., "Cardiovascular safety of anagrelide in healthy subjects: Effects of caffeine and food intake on pharmacokinetics and adverse reactions," Clinical Drug Investigation 33:45-54 (2013).

Watson et al., "Anagrelide is an anti-megakaryocytic and not an anti-platelet agent," Platelets, 30(1): 136-137 (2019).

* cited by examiner

USE OF ANAGRELIDE FOR TREATING CANCER

RELATED APPLICATIONS

This application is a § 371 national stage application based on Patent Cooperation Treaty Application serial number PCT/GB2015/054116, filed Dec. 22, 2015; which claims the benefit of priority to GB 1422978.5, filed Dec. 22 2014.

FIELD OF THE INVENTION

The present invention relates to the use of the anti-megakaryocytic agent anagrelide or a therapeutically active metabolite thereof, in the prevention and/or treatment of metastatic disease in cancer patients displaying paraneoplastic thrombocytosis. In particular the invention relates to reducing the formation and progression of potentially fatal bone, lung and other metastases most evident in such patients.

The present invention also relates to the use of the anti-megakaryocytic agent anagrelide or a therapeutically active metabolite thereof, for enhancing the efficacy of conventional cancer chemotherapeutic drugs in thrombocytotic cancer patients.

The drug may be formulated in an appropriate side-effect modulating (SEM)/cardiac-sparing formulation, which minimises the PDEIII inhibitory actions and thereby cardiostimulant activity of the drug. Suitable formulations include those previously established to reduce or avoid first pass metabolism and thus, in this case, the generation of anagrelide's highly potent PDEIII inhibitory cardioactive metabolite. Such preparations have the potential to inhibit platelet-mediated cancer cell proliferation, tumour development and formation of cancer metastases without the unwanted cardiotoxicity usually associated with anagrelide.

BACKGROUND TO THE INVENTION

Despite significant advances in the treatment of cancer over the last 25 years, the survival rates in several cancers remains dismally low. For example the five year survival rates for stomach, brain, and oesophageal cancers are of the order of 15-20% while lung and pancreatic cancer are less than 10% (Cancer Research UK data, 2010 http://www.cancerresearchuk.org/health-professional/cancer-statistics/survival).Even amongst the more common cancers, for example bowel and bladder cancer, survival rates are only around 50%.

In recent years it has been observed that cancers of various diverse types are associated with a thrombocytosis i.e. an elevation of blood platelets. While this so-called paraneoplastic thrombocytosis was first noted by Reiss et al as far back as 1872, it is only recently that thrombocytosis has been identified as an independent risk factor for aggressive cancer progression, metastatic disease and poorer survival. Paraneoplastic thrombocytosis is observed in some 10-57% of patients with cancer with the number varying depending on cancer cell type (Sierko & Wojtukiewicz 2004) and disease stage. For example, the proportion of cancer patients affected by thrombocytosis has been reported to be 33% in ovarian cancer (Hale, 2012), 18% in breast cancer (Stravodimou & Voutsadakis, 2013), 21% in oesphageal cancer (Voutsadakis, 2014), 21% in stomach cancer (Wang et al, 2012), 27% in lung cancer (Maraz et al, 2013) 14% in colorectal carcinoma (Guo et al, 2014), 12.5% in kidney cancer (O'Keefe et al, 2002) and 3% in liver cancer (Hwang et al, 2004). In these and other solid cancers, patients with paraneoplastic thrombocytosis have shown a poorer response to standard of care anti-cancer therapy and significantly worse survival compared to patients with a normal platelet count. In particular this patient subgroup is frequently susceptible to bone metastases which are associated with the poorest prognosis (Zhang et al 2015). This suggests that these patients are under-served by currently available treatments.

The influence of platelet count on cancer outcomes is clearly evident in, for example, patients with gastric carcinoma where the five year survival rate was shown to be only 16% in patients with higher platelet counts (>300,000/uL) compared to 63% in patients with lower numbers (<300,000/uL) (Lv et al, 2010). In lung cancer patients too, the 3-year cumulative overall survival (OS) probability was lower (59.2%) for patients with elevated platelet counts compared to patients with normal platelet counts (75.3%) (Yu et al, 2013). In patients with glioblastoma, higher platelet counts also correlated with poorer clinical outcomes (Williams, 2012). Similarly in extensive investigations in both murine and human ovarian cancer, Stone et al (2012) concluded that paraneoplastic thrombocytosis fuels aggressive tumour growth and poorer survival. Very recent studies have shown a primary role for platelets in stimulating the growth of multiple myeloma cells as well as tumour growth (Takagi et al 2015). In platelet depleted mice decreased tumour growth was evident along with improved survival.

While there is little evidence that platelets are abnormal in cancer, there is compelling evidence that cancer cells stimulate the over-production and inappropriate activation of platelets creating a favourable micro-environment for tumour growth and metastasis. Over 30 growth-regulatory proteins including transforming growth factor β (TGFβ), vascular endothelial growth factor (VEGF), platelet factor 4 (PF4) and platelet derived growth factor (PDGF) are stored within the cytoplasmic granules of platelets while signaling receptors pack the cell membrane which normally guide growth factor release in their core functions of haemostasis, angiogenesis and tissue healing. Cancer cells interact directly and indirectly with platelets in multiple ways to hijack this armament of angiogenic, lymphangiogenic and general mitogenic factors to enhance tumor expansion and metastatic spread (Davis et al, 2014; Bambace & Holmes, 2011; Buergy et al, 2012; Labelle & Hynes, 2012; Riedl et al, 2014).

Several recent scientific reviews and conferences have highlighted the multiple interactions that occur between platelets and cancer cells (Bambace and Holmes (2011), Stravodimou & Voutsadakis (2013), Labelle et al (2011), Riedl et al (2014), 55th ASH meeting December 2013. Cancer cells themselves appear to stimulate thrombocytosis with enhanced numbers of activated platelets acting back on cancer cells to aid the development and spread of cancer.

This platelet-cancer cell interaction leads to a "vicious cycle" or pathogenic loop involving a symbiotic relationship between the two. Cancer cells stimulate megakaryocyte/platelet production which in turn, through release of various growth factors, enhances cancer cell growth and multiplication and ultimately metastasis. The increased number of cancer cells then drives more platelet formation and so on in a pathogenic feedback loop (Lin R J et al 2014).

The initial stimulation of megakaryocytopoiesis is generally thought to be effected by cancer cell cytokine release which stimulates the liver to produce thrombopoietin the driver of the process of platelet production. The resultant increase in platelet numbers (thrombocytosis) and consequent greater availability of platelet-derived nutrient growth factors TGFβ, PF4, VEGF, and PDGF, then stimulates cancer cell growth and multiplication. Furthermore VEGF promotes angiogenesis and formation of anchoring blood vessels and so establishment of the primary tumour.

As the number of cancer cells grow this in turn stimulates greater megakaryocytopoiesis and the formation of more platelets which are activated by cancer cells. Once activated these platelets adhere to circulating cancer cells which have become detached from the primary tumour and afford shielding from the immune system's natural killer cells. This protection enables the circulating cancer cells to reach other target organs such as the bone where secondary tumours or metastases may develop.

There is now substantial evidence for this proposed sequence of events. For example evidence that platelets enhance cancer cell growth in ovarian cancer via a transforming growth factor β (TGF-β) dependent mechanism was reported by Cho et al (2012). Platelets are the major source of TGF-β in the circulation and as such are therefore very likely to stimulate cancer cell proliferation.

As mentioned earlier, subsequent tumour development and growth is dependent on the formation of new blood vessels (angiogenesis), first postulated by Folkman in 1971, and platelets are carriers of a variety of factors that regulate this process. These factors are stored in the a granules of platelets and are released after platelet activation brought about by cancer cells. The most prominent and important of these factors for angiogenesis is VEGF. Cancer cells appear to specifically induce the release of VEGF from the a granules which then promotes angiogenesis (Kisucka et al, 2006) and so tumour establishment and growth.

The evidence supporting a promotional effect of platelets on tumour spread (metastasis) is now compelling (Gay & Felding Habermann (2011); Borsig (2008)). Since more than 90% of all cancer associated deaths are caused by metastasis, (Lou et al, 2015) understanding the role of platelets in this process becomes key. During metastasis, cancer cells disseminate to other parts of the body by entering the bloodstream from the primary tumour in a process called intravasation which is now known to be mediated by platelets (Battinelli et al, 2014). Once cancer cells have entered the blood they activate platelets enabling the latter to aggregate and form a shield around the circulating tumour cells which affords protection against the immune system's natural killer (NK) cells (Nieswandt et al, 1999). The mechanism whereby this interaction between cancer cells and platelets is effected is not completely understood but is considered to involve a number of mechanisms including platelet surface integrins and their corresponding tumour cell ligands and by the binding of platelet P-selectin with selectin ligands expressed on tumour cells (Amo L et al, 2014). Those circulating cancer cells escaping destruction by NK cells ultimately extravasate the vasculature at metastatic sites by attaching to endothelial cells that line blood vessels and crossing the vessel walls of tissues or organs. This process of extravasation is facilitated by platelet release of adenosine triphosphate so opening the endothelial barrier and enabling tumour cells to escape the vasculature (Schumacher et al, 2013). Further facilitating this process of extravasation and penetration of cancer cells into adjacent tissue is their transformation to a more malignant phenotype, the so-called "epithelial mesenchymal transition" (EMT) which has again recently been shown to be dependent on platelet/cancer cell interactions (Labelle et al, 2011). Platelet-derived TGFβ in this interaction synergistically activates the TGFβ/Smad and NF-κB pathways in the cancer cells, resulting in EMT transition. Inhibition of NF-κB signaling in cancer cells or ablation of TGFβ1 expression solely in platelets has been shown to protect against lung metastasis in vivo (Labelle et al, 2011). Thus cancer cells would appear to rely on platelet-derived signals outside the primary tumour for efficient metastasis. Indeed thrombocytosis is most frequently observed in patients with metastatic cancers.

Bone metastases are a frequent complication of many cancers (notably breast, prostate, lung, thyroid and kidney) and, as well as resulting in very severe pain, are usually fatal (VVeilbaecher et al 2011). Since the late nineteenth century, it has been thought that the microenvironment of the local host tissue actively participates in the propensity of certain cancers to metastasize to specific organs including the development of "premetastatic niches", and that bone provides an especially fertile 'soil' (Paget 1889). Migration and retention of tumour cells in bone marrow is effected by multiple binding interactions including those with surface integrins on both tumor cells and the supporting host stromal cells in bone (osteoclasts/osteoblasts, new blood vessels, inflammatory cells, megakaryocytes/platelets and bone marrow stromal cells) which plays a key role in enhancing bone metastasis.

Furthermore in thrombocytotic cancer patients, higher levels of megakaryocytes—and their subsequent development into platelets—are evident at the site of their production in bone marrow and appear to predispose these patients to a greater risk of bone metastasis. In a recent paper by Zhang et al (2015) a strong correlation was found between thrombocytosis in pulmonary adenocarcinoma patients and the development of bone metastasis. As the first cells to be encountered by extravasating tumour cells reaching the bone marrow, megakaryocytes have been reported to have an apoptopic/phagocytotic effect on cancer cells and act in a defensive capacity (Park et al 2011. Li et al 2011 & Jackson et al 2015). However running counter to this is the production of the megakaryocyte secreted growth factors including TGFβ, VEGF & PDGF etc. which are known to stimulate cancer cell growth. Furthermore and self-evidently, the very development of bone metastases speaks to the limitations of any defensive role which may be played by megakaryocytes. Pivotal evidence for the critical role of megakaryocytes/platelet in promoting breast cancer skeletal metastasis was reported back in 2004 by Boucharaba et al and also by Gupta & Massague in the same year. While megakaryocytes may initially exhibit a defensive role, the homing of cancer cells towards bone marrow and encounters with megakaryocytes, via a complex multistep process (Mishra et al 2011), leads to disturbance of osteoblast/osteoclast bone homeostasis (Weilbaecher et al 2011), a process normally regulated, in part, by megakaryocytes (Kacena et al 2006). The overwhelming numbers of cancer cells entering the bone marrow as a result of this chemotaxis may subsequently lead to the development of bone metastases. On balance therefore it would appear that the excessive numbers of megakaryocytes evident in thrombocytotic patients support the development of bone metastases.

Other than the bone marrow, another major reservoir for megakaryocytes is the lungs. Here too it has been reported that the numbers of pulmonary megakaryocytes associated with lung metastases are higher than in the lungs from patients with localized carcinomas and healthy individuals, once again pointing to a critical role for megakaryocytes in the development of metastases (Soares 1992).

It would therefore appear that cancer associated thrombocytosis plays a critical role in the disease outcome in terms of tumour cell growth, tumour establishment and importantly subsequent metastasis particularly in bone and lung. Therapeutic interventions to reduce the function and/or formation of platelets may therefore offer a valuable new approach to tackling the morbidity and mortality associated with cancer One approach to addressing the problems posed by this excessive number of platelets thrombocytotic patients is the use of so-called "anti-platelet" agents. This term is somewhat confusing since such agents do not actually reduce platelet numbers but simply reduce platelet activation and aggregation. This has the potential to reduce the immune shielding offered by platelets and the subsequent vascular deposition of cancer cells. In a retrospective observational study, following indeterminate exposure to a variety of anti-aggregatory agents including cilostazol, clopidogrel, prasugrel, ticlopidine, abciximab, eptifibatide, tirofiban, anagrelide, aspirin, & dipyridamole Rachidi et al (2014) noted an apparent association between improved treatment outcomes in head and neck cancer and such treatment in general. However improved survival was most notably associated with those patients exhibiting lower platelet counts which would not have been brought about by these anti-aggregatory agents (with the sole exception of anagrelide) although these authors confusingly describe their use as "a pharmacologic intervention to lower platelets". In an earlier paper Ambrus et al (1986) reported that anti-aggregatory therapy in mice with anagrelide, a drug having anti-aggregatory but no platelet lowering effects in animals (it's platelet-lowering actions being specific to humans), was associated with an increase in circulation time of cancer cells, an indicator of the reduced potential for development of metastasis. While such anti-platelet therapy has been recently shown to play a useful part in cancer prevention (Bosetti et al, 2012, Leader et al 2015) for example with aspirin in bowel cancer, the potential value of selective platelet lowering agents in arresting the progression of cancer has not been systematically investigated. That said the human platelet lowering/anti-aggregatory agent anagrelide was employed in a clinical case study reported by Voglova et al (2006) in which platelet reduction was attempted in a 51-year old man treated with imatinib and anagrelide. Here however, the principal objective was to minimise serious thrombo-hemorrhagic complications associated with his chronic myeloid leukemia rather than cancer progression. Another clinical case study (Chen Y G et al 2012) in a 57-year old male patient used anagrelide's platelet lowering activity to mitigate the thrombotic risk in primary pulmonary neoplastic thrombocytosis. Success was measured by a reduction in thrombosis induced leg swelling and not cancer progression.

Platelet lowering, as an alternative to one of simply modifying platelet aggregation, offers an attractive strategy to slowing cancer progression. Concern over any possible bleeding risks potentially associated with a modest platelet reduction are likely to be misplaced since haemostasis is essentially unaffected even when platelet numbers are reduced to 100,000/µL. Indeed surgeons will frequently operate, without platelet transfusion, at platelet counts above 75,000/µL. Prophylactic platelet transfusion before surgery is only recommended in severely thrombocytopenic patients to raise the platelet count to between 50,000 and 100,000/µL if possible. Surgery and other invasive procedures have been performed at lower platelet counts without major bleeding, see:
http://www.transfusionguidelines. org/?Publication=HTM&Section=9&pageid=1120. There is therefore considerable scope to reduce platelet numbers without incurring a bleeding risk.

In animals platelet depletion in tumour bearing mice has been shown to trigger intra-tumour haemorrhage and consequent tumour necrosis (Ho-Tin-Noe et al, 2009). Furthermore depletion of platelets has been shown to enhance the therapeutic anti-tumour effects of a DNA vaccine for cancer (Lee et al, 2013). Additional support for the potential value of platelet depletion in the treatment of cancer comes from further animal studies where experimental reduction in platelet number has been shown to have profound anti-metastatic effects (Gay & Felding-Habermann, 2011). Also Stone et al (2012) showed that eliminating thrombocytosis in mice with ovarian cancer inhibited tumour growth and increased tumour necrosis. While there are several other published studies highlighting the importance of platelet count in cancer progression [Demers et al (2011), Li et al (2014) and Cho et al (2012)] none specify how this might be achieved with, for example, the anti-megakaryocytic agent anagrelide, nor how the profound anagrelide-induced cardiac stimulation might be avoided.

One approach to lowering platelets derives from an understanding of the mechanism by which cancer cells induce thrombocytosis. Although Buergy et al speculated on possible direct stimulation of megakaryocytes by cancer cells, other evidence suggests an indirect mechanism. This is believed to be effected by increased circulating levels of cytokines such as interleukin IL-1, IL-6, IL-8 and/or granulocyte-colony stimulating factor (Sierko & Wojtukiewicz 2004, Johnson et al 2015) which induce thrombopoietin production in the liver, and which in turn stimulates platelet generation in the bone marrow. In a recent study in mouse models of ovarian cancer, administration of the IL-6 antibody, siltuximab, significantly reduced platelet count and tumour growth (Stone et al, 2012). However the use of such preparations may be limited by their cost, the requirement for intravenous delivery, and particularly their marked immunosuppressant as well as other unwanted side-effects. The most prominent side-effects associated with siltuximab and indeed tocilizumab, another IL-6 antibody preparation, are upper respiratory infections (>20% of patients with siltuximab). In cancer patients with compromised immune systems these are particularly undesirable side-effects. Indeed serious and sometimes fatal infections have been reported in patients receiving such immunosuppressive agents. See: http://www.medicines.org.uk/emc/ingredient/2423/tocilizu mab/

An alternate approach to platelet reduction might be to employ one or more of the drugs that are usually used to treat essential thrombocythemia (ED, a rare myeloproliferative condition marked by excessive numbers of blood platelets and consequential thrombotic risk. Here the platelet count may be greatly in excess of $10^6$ platelets/µL blood compared to the normal range of 150,000-350,000 platelets/µL. Treatment of this condition has historically used one or more of the following agents:—

Hydroxycarbamide (Hydroxyurea).

This is a non-specific cytotoxic agent affecting several haematopoietic cell lines including granulocyte, leucocyte and erythrocyte lineages. Leucopenia, a potential consequence of administration of hydroxcarbamide, would be undesirable in cancer patients who may already have a compromised immune system.

See: http://www.medicines.org.uk/emc/medicine/18928/SPC

Busulphan

This is an alkylating chemotherapeutic agent. Toxicities includes severe emesis, wasting syndrome, seizures, and hepatic toxicity (veno-occlusive disease, VOD). Seizures and VOD are serious concerns with busulphan therapy and the latter results in dose-limiting toxicity. Thus in view of such serious side-effects busulphan may not be a drug of choice to lower blood platelets in cancer patients.

See: http://www.medicines.orq.uk/EMC/medicine/24686/SPC/Busulfan+2+mg+tablets/

Interferon-Alpha

While this drug will reduce blood platelet numbers it is expensive, only available as an injectable preparation, and has significant side-effects including leucopenia, myalgia, arthralgia and anorexia, again all highly undesirable in cancer patients. See:http://www.medicines.org.uk/emcsearchresults.aspx?term=Interferon%20alfa2b%20(Intron-A)s.

Anagrelide

This drug is the only cytoselective platelet lowering agent currently available i.e. it does not inhibit the formation of other blood cell lines apart from platelets (Hong et al 2006). This unique selectivity would be particularly valuable in treating cancer patients who may already be haematologically compromised being potentially both anaemic and leukopenic. Angrelide is currently marketed as Agrylin®, Xagrid® and Thromboreductin® as well as various generic formulations for the treatment of essential thrombocythemia. The primary pharmacological effects of this drug i.e. platelet lowering, is brought about by its effects on the maturation of megakaryocytes, the progenitors of platelets. As stated above its cytoselective actions makes it uniquely valuable. However the drug also demonstrates anti-aggregatory (anti-platelet) activity, as the result of inhibition of phosphodiesterase (PDE) III, which is a secondary but separate pharmacological activity. It is regrettably this property, namely inhibition of PDEIII, which also results in its highly undesirable cardiovascular side-effects.

It now appears that anagrelide's unwanted cardiovascular effects are largely due to an extremely potent PDEIII inhibitory metabolite of the drug, namely 3-hydroxy anagrelide (formerly known as BCH 24426). As a positive inotrope this compound has a marked stimulatory effect on the heart (Wang et al, 2005). While anagrelide itself has some PDEIII inhibitory activity, its activity compared to this metabolite is comparatively low with the latter being nearly 40-fold more potent but having a platelet lowering activity somewhat less than anagrelide itself (Wang et al, 2005). The formation of this metabolite is the result of extensive first pass metabolism after oral dosage. In clinical practice plasma concentrations of this metabolite typically exceed those of the parent drug by 2-3-fold (Martinez-Selles et al, 2013).

These adverse cardiovascular effects which manifest as tachycardia, palpitations and severe headache can be dose-limiting and are the primary cause of patients discontinuing therapy. It is conservatively estimated that some 25% of patients on anagrelide discontinue drug treatment as a result of such cardiovascular side-effects (Birgegard et al, 2004). The approved labeling for anagrelide makes clear that cardiovascular effects, such as palpitations and tachycardia, may occur after therapeutic doses of the drug especially if given to patients with pre-existing heart disease. Accordingly the labeling warns against administering the drug to such patients and recommends a cardiovascular examination before starting therapy see:—
http://www. medicines.org uk/emdmedicine/15737/SPC/Xagrid+0.5 mg+hard+capsule These cardiovascular side effects currently relegate anagrelide's use to second line therapy in the treatment of essential thrombocythemia (see Birgegard et al, 2004).

Several literature reports have further highlighted the cardiac complications that may be associated with anagrelide's chronic use (Mlot & Rzepecki 2012). In one case study anagrelide's cardiotoxicity manifested as congestive heart failure in a 48-year-old woman with polycythemia vera (James CW 2000). During routine treatment the frequency of such cardiovascular side-effects has been reported as follows:—

Common: palpitations and tachycardia,

Less common: congestive heart failure, hypertension, arrhythmia, atrial fibrillation Occasionally: angina, myocardial infarction, cardiomegaly, cardiomyopathy, pericardial effusion, and orthostatic hypotension.

In a study reported by Jurgens et al (2004), anagrelide was found to cause cardiomyopathy in a number of patients. In data collected from some 434 patients with essential thrombocythaemia and polycythemia vera, idiopathic cardiomyopathy was evident in 11. Another case of anagrelide induced cardiomyopathy was later reported by Wong et al (2008). Furthermore a recent communication (Shire, 2013) sent out by the drug's originator's, Shire Pharmaceuticals, to all healthcare professionals has highlighted the fact that serious cardiovascular adverse events may occur even in patients without suspected heart disease and with normal previous cardiovascular function.

Cardiovascular side-effects would be problematic in cancer patients who are potentially at risk of chemotherapy-induced cardiovascular toxicity, particularly those elderly patients with pre-existing cardiovascular disease (Yeh et al 2004). In an in-depth review of the cardiotoxicity of oncologics, Fuiza M (2012) highlighted this to be a common problem with most, if not all, chemotherapeutic agents. Indeed chemotherapy is now widely recognised as being associated with many different aspects of cardiotoxicity ranging from arrhythmias, pericarditis, myocardial ischemia to cardiomyopathy (Saidi & Althrethi, (2011), Mlot & Rzpecki 2012). Many of the commonly used chemotherapeutic agents such as cisplatin, doxarubicin, and trastuzumab have been shown to have a marked adverse effect on left ventricular function (Saidi & Althrethi, 2011).

Thus despite the considerable potential utility of anagrelide to selectively lower platelets in thrombocytotic cancer patients, its use appears to have been overlooked possibly due to concern over exacerbation of any cardiotoxicity induced by chemotherapy.

Despite these concerns three patents have recently appeared suggesting that anagrelide could potentially be used as an anti-tumour agent in cancer patients through either its supposed apoptotic effects at very high doses or, and rather surprisingly, its PDEIII inhibition. In WO2014/183673 A1 Quiang Yu et al claim "antitumor use of anagrelide and derivatives" based on the apparent apoptosis seen in vitro in various cancer cell lines (IC50 value 100 nM) and in vivo studies showing such activity in rats after doses of 10-30 mg/kg. These concentrations/doses are >10-fold & >1000-fold higher than could be safely achieved in man and would result in profound cardiovascular disturbance. Additionally other published studies have found no apoptopic effects of anagrelide even up to concentration of 1 µM (Hong et al 2006). In two other patents, WO2015/055898 and WO2014/164794, the exploitation of anagrelide's PDEIII inhibitory action is claimed as useful in treating cancer. In the light of the clinical concerns over the cardiovascular problems already evident in cancer patients such proposals would seem particularly inappropriate.

In summary the limited effectiveness of currently available cancer treatments highlights the need for a new approach to addressing this disease. Recent clinical data drawing attention to the role of platelets in promoting cancer cell growth, tumour establishment and metastasis particularly in bone offers a potentially new approach for therapeutic intervention. At its simplest this might just involve reduction in platelet numbers. However blocking cancer cell-induced stimulation of platelet production and hence disruption of the pathogenic loop between cancer cells and platelets would offer an intriguingly different approach to cancer treatment. Furthermore inhibition of cancer cell migration to bone marrow would offer a potential target to minimise the risk of the almost inevitably fatal bone metastases.

The only cytoselective platelet lowering agent currently available is anagrelide which would, in its present form, be an unsuitable drug candidate due to its highly undesirable cardiovascular side-effects which could put at further risk cardio-compromised cancer patients.

SUMMARY OF THE INVENTION

There is now extensive clinical evidence highlighting the presence of thrombocytosis in many different cancers and the role that excessive numbers of platelets play in promoting cancer cell growth, tumour establishment including angiogenesis and subsequent metastasis, particularly potentially fatal bone metastases. Since cancer cells stimulate megakaryocytopoiesis/platelet production which in turn drives cancer cell growth, this leads to a vicious cycle or pathogenic loop being established.

Paraneoplastic thrombocytosis therefore presents a potentially valuable new target for therapeutic intervention and offers the opportunity to break this vicious cycle. Despite this, no drugs are currently employed for this purpose in cancer treatment possibly due to the lack of safe cytoselective anti-megakaryocytic agents. Of the few currently available platelet lowering agents, anagrelide, inhibiting just platelet formation and no other haematopoietic cell lines, is uniquely valuable.

According to an aspect of this invention there is provided a compound, wherein the compound is anagrelide, a pharmaceutically acceptable salt, solvate or active metabolite thereof, for use in treating or preventing metastatic disease in a thrombocytotic cancer patient.

According to an aspect of this invention there is provided a method of treating or preventing metastatic disease in a thrombocytotic cancer patient, the method including administering to the patient a compound, wherein the compound is anagrelide, a pharmaceutically acceptable salt, solvate or active metabolite thereof.

A thrombocytotic patient is an individual having a high blood platelet count, for example, a patient having a blood platelet count of >450,000/ µL blood (Harrison et al, 2010). However, for individuals whose baseline platelet counts is in the lower range of normal, a platelet count above 400,000/ µL, 350,000/ µL, 300,000/ µL, or even 250,000/ µL may be considered thrombocytotic.

In another aspect of this invention there is provided a compound, wherein the compound is anagrelide, a pharmaceutically acceptable salt, solvate or active metabolite thereof, for use in inhibiting the stimulatory effect of cancer cells on the process of megakaryocytopoiesis.

In another aspect of this invention there is provided a method of inhibiting the stimulatory effect of cancer cells on the process of megakaryocytopoiesis in a patient, the method including administering to the patient a compound, wherein the compound is anagrelide, a pharmaceutically acceptable salt, solvate or active metabolite thereof. In an embodiment, the patient is a thrombocytotic cancer patient.

Breaking this vicious cycle or pathogenic loop which fuels cancer growth and development, offers a radically new approach to treatment of the disease.

In another aspect of this invention there is provided a compound, wherein the compound is anagrelide, a pharmaceutically acceptable salt, solvate or active metabolite thereof, for use in inhibiting the migratory attraction of circulating cancer cells towards megakaryocytes.

In another aspect of this invention there is provided a method of inhibiting the migratory attraction of circulating cancer cells towards megakaryocytes in patient, the method including administering to the patient a compound, wherein the compound is anagrelide, a pharmaceutically acceptable salt, solvate or active metabolite thereof. In an embodiment, the patient is a thrombocytotic cancer patient.

Inhibition of the migratory attraction of circulating cancer cells towards megakaryocyte limits the possibility of metastases, for example, in bone and lung, the principal repositories of megakaryocytes in the body. Blocking this 'fatal attraction' again offers a radically different approach to the treatment of cancer.

In one embodiment of the invention, the cancer to be treated is selected from the group consisting of brain, oral cavity, the head and neck including the nasopharanygeal region, thyroid carcinoma, gastrointestinal cancers including oesophageal or gastric cancer, pancreatic, hepatocellular or colorectal cancer as well as cancer of the lungs and bronchus, and cancer of the ovaries, endometrium, cervix, breast, prostate, kidneys, skin mesothelioma, melanoma, gallbladder or in multiple myeloma.

In an embodiment, the cancer is selected from the group consisting of ovarian and breast cancer In an embodiment, the cancer is selected from the group consisting of cancer of the brain, oral cavity, the head and neck including the nasopharanygeal region and thyroid carcinoma.

In an embodiment, the cancer is selected from the group consisting of ovarian cancer, oesophageal, gastric and colorectal cancer.

In an embodiment, the cancer is selected from the group consisting of cancer of the gastrointestinal tract including oesophageal, gastric, pancreatic, hepatocellular or colorectal cancer.

In an embodiment, the cancer is selected from the group consisting of: ovarian cancer, lung cancer, oesophageal cancer, gastric cancer.

In an embodiment, the cancer is selected from the group consisting of cancer of the lungs and bronchus.

In an embodiment, the cancer is selected from the group consisting of: pancreatic cancer, colorectal cancer and renal cancer.

In an embodiment, the cancer is selected from the group consisting of: head and neck cancer, hepatocellular cancer.

In an embodiment, the cancer is selected from the group consisting of cancer of the ovaries, endometrium, cervix or breast.

In an embodiment, the cancer is selected from the group consisting of the prostate.

In an embodiment, the cancer is selected from the group consisting of: cancer of the brain, oral cavity, cancer of the bronchus, endometrium, breast, prostate, skin mesothelioma and melanoma.

In an embodiment, the cancer is selected from the group consisting of cancer of the kidneys or gallbladder.

In an embodiment, the cancer is multiple myeloma.

In an embodiment, the patient being treated is a thrombocytotic individual who is at risk of developing cancer.

In an embodiment, the patient being treated is a thrombocytotic cancer patient.

In another embodiment the patient being treated is a cardio-compromised and thrombocytotic cancer patient In an embodiment, the patient being treated is at a particular genetic risk of specific cancers, e.g. breast and ovarian cancer carriers of the BRCA1/2 genes.

In an embodiment of this invention, anagrelide, a pharmaceutically acceptable salt, solvate or active metabolite thereof is formulated to minimise any cardiovascular side-effects in an appropriate cardiac sparing preparation. Such a formulation may be achieved by controlling the rate and extent of formation of the first pass generated highly potent cardioactive metabolite, 3-hydroxy anagrelide, by minimising the proportion of drug absorbed through the liver so reducing the risk of undesirable inotropic and vasodilatory effects. In so doing this enables the safer use of the drug in preventing or treating cancer in thrombocytotic patients (see definition).

Those skilled in the art will appreciate there are numerous well established strategies and methods available for reducing or avoiding first pass metabolism and so, in the case of anagrelide, the generation of its highly potent cardioactive metabolite.

Enteral dosage formulations that exploit absorption at the extreme proximal and distal ends of the GI tract reduce the proportion of drug passing through the liver and hence first pass effect. For example buccal lozenges—hard sugar formulations that dissolve slowly in the mouth—facilitate buccal and sublingual absorption and consequently passage of the drug directly into the systemic circulation. Such formulations would reduce the amount of drug reaching the lower GI tract where it would normally be absorbed and pass through the liver with the consequential first pass generation of anagrelide's cardio-active metabolite.

Alternate buccal formulations include mucoadhesive buccal film and tablets, sublingual tablets, oromucosal sprays etc, many of which have been successfully employed with various drugs to reduce first pass metabolism e.g. testosterone http://www.actientpharma.com/filebin/pdf/products/5881610_Striant_full_PI_4pager. and buprenorphine (Krotscheck et al, 2010).

Drug delivery to the distal end of the GI tract (rectum) results in partial absorption by the inferior and middle haemorrhoidal veins which drain directly into the vena cava, and hence systemic circulation so reducing delivery though the liver and consequential marked first pass generation of anagrelide's cardioactive metabolite. Such location specific drug delivery is readily achievable with rectal gels or suppositories.

Parenteral administration—avoiding the GI tract altogether affords the most direct means of circumventing the first pass generation of anagrelide's highly cardioactive metabolite. Generic descriptions of the various possible parenteral formulations are comprehensively covered in Remington, The Science and Practice of Pharmacy, $22^{nd}$ Edition, 2012.

One attractive non-enteral route of administration reducing the risk of formation of this first pass metabolite is the use of an intranasal spray. Here drug is absorbed via the nasal mucosa directly into the systemic circulation again minimising first pass hepatic metabolism. This well established strategy has been successfully used for the systemic delivery of a number of medications including midazolam and desmopressin.

Another means of minimising formation of this cardioactive metabolite is to use the pulmonary route of administration. Aerosol administration to the pulmonary epithelium for systemic action would again overcome the issue of first pass metabolism in the liver.

A further non-enteral route is afforded by topical/dermal application. Here the drug is absorbed directly through the skin into the systemic circulation so, once again, avoiding first pass formation of anagrelide's cardioactive metabolite.

The formulations of the present invention may be administered ideally once or twice daily but others may benefit from less or more frequent administration. In all of these dosage forms the essence is to reduce the formation of anagrelide's cardioactive metabolite, 3-hydroxy anagrelide using well established approaches. Co-administration with other anticancer drugs and adjunctive therapy is also envisaged.

DETAILED DESCRIPTION OF THE INVENTION

Definitions as used herein:—

Figure 1:
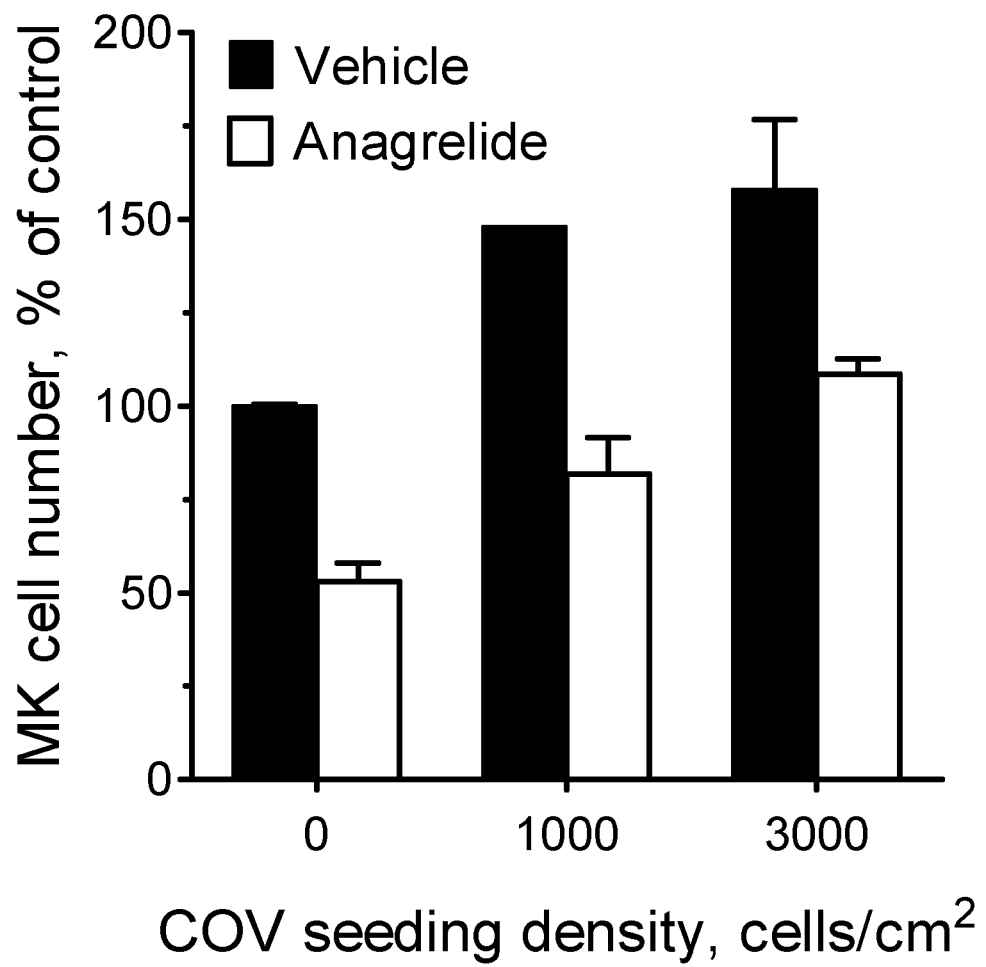
FIG. 1. Ovarian cancer cells enhance megakaryocyte development: Inhibiting action of anagrelide. Expanded CD34+ cells were co-cultured for 7 days in MK medium containing 10 ng/ml TPO with or without anagrelide (1 µM) and in the absence or presence of COV362 cells seeded at the indicated densities. Co-culture was carried out in a Boyden chamber with COV362 cells seeded in the bottom compartment 4 days prior to the beginning of the differentiation period. MK development was analysed as described under Experimental Procedures. Results (mean±SEM of 2 replicate cultures) are expressed relative to the number of megakaryocytes developed in the absence of COV362 cells.

Anti-megakaryocytic refers to platelet lowering activity in humans by interfering with megakarocyte development and maturation into blood platelets. Such agents may be particularly valuable in the prophylaxis and treatment of cancer.

"Thrombocytosis" is defined by World Health Organization as a platelet count greater than 450,000/ μL blood (Harrison et al, 2010). However a lower number may be relevant in the therapeutic setting described herein. In such subjects platelet counts of 350,000/ μL or even 300,000/ μL may be considered as being thrombocytotic. In other subjects, a platelet count of 250,000/ μL may be considered as being thrombocytotic for the purposes of this invention.

"Cardio-compromised" is a general term for any heart problem, such as coronary artery disease, atherosclerosis, arteriosclerosis, aneurysm, dysrhythmia, heart failure, myocardial ischemia/infarction, hypertension and thromboembolism. More specifically it can refer to reduction in left ventricular function frequently seen in cancer patients treated with chemotherapy agents.

The term "side-effect modulated" or "cardiac-sparing" refers to those formulations (and their routes of administration) of anagrelide or an active metabolite of the drug which are specifically designed to minimise the first pass generation and subsequent systemic exposure to the potent cardioactive agent 3-hydroxy anagrelide or other similar entities.

Thrombocytopenia is usually defined as a platelet count less than 75,000/μL.

The term "carrier" refers to a diluent, excipient, and/or vehicle with which anagrelide (or appropriate active metabolite thereof) is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" edited by Loyd V Allen, 22nd Edition, 2012).

The phrase "pharmaceutically acceptable" refers to molecular entities and compositions that are generally regarded as safe. In particular, pharmaceutically acceptable carriers used in the practice of this invention are physiologically tolerable and do not typically produce an allergic or similar untoward reaction (for example, gastric upset, dizziness and the like) when administered to a patient. Preferably, as used herein, the term "pharmaceutically acceptable" means approved by a regulatory agency of the appropriate governmental agency or listed in the U.S. Pharmacopoeia or other generally recognized pharmacopoeia for use in humans.

A "pharmaceutically acceptable excipient" means an excipient that is useful in preparing a pharmaceutical composition that is generally safe, non-toxic and neither biologically nor otherwise undesirable, and includes an excipient that is acceptable for human pharmaceutical use. A "pharmaceutically acceptable excipient" as used in the present application includes both one and more than one such excipient.

The term "treating" includes: (1) preventing or delaying the appearance of clinical symptoms of the state, disorder or condition developing in a person who may be afflicted with or predisposed to the state, disorder or condition but does not yet experience or display clinical or subclinical symptoms of the state, disorder or condition; (2) inhibiting the state, disorder or condition (e.g., arresting, reducing or delaying the development of the disease, or a relapse thereof in case of maintenance treatment, of at least one clinical or subclinical symptom thereof); and/or (3) relieving the condition (i.e., causing regression of the state, disorder or condition or at least one of its clinical or subclinical symptoms). The benefit to a patient to be treated is either statistically significant or at least perceptible to the patient or to the physician. In an embodiment, the term "treating" includes reducing the potential for any or all of the following: cancer cell proliferation, tumour establishment and development and the formation of metastases.

The term "subject" refers to humans.

"Effective amount" means an amount of anagrelide (or appropriate active metabolite thereof) or composition of the present invention sufficient to result in the desired therapeutic response. The therapeutic response can be any response that a user (e.g., a clinician) will recognize as an effective response to the therapy. The therapeutic response will generally be amelioration of one or more of the conditions treatable with the active drug. For example, slowing of tumour development and metastasis in a patient. It is further within the skill of one of ordinary skill in the art to determine appropriate treatment duration, appropriate doses, and any potential combination treatments, based upon an evaluation of therapeutic response.

The term "active ingredient," unless specifically indicated, is to be understood as referring to anagrelide or any appropriate active metabolite thereof. The term "active metabolite" refers to anagrelide which has been hydroxylated at either positions 5, 8 or 9 singly or in combination. Alternatively oxidation at the tertiary nitrogen position forming an N-oxide is envisaged with or without hydroxylation as positions 5, 8 or 9.

The term "salts" can include acid addition salts or addition salts of free bases. Suitable pharmaceutically acceptable salts include, but are not limited to, metal salts such as sodium potassium and cesium salts; alkaline earth metal salts such as calcium and magnesium salts; organic amine salts such as triethylamine, guanidine and N-substituted guanidine salts, acetamidine and N-substituted acetamidine, pyridine, picoline, ethanolamine, triethanolamine, dicyclohexylamine, and N,N'-dibenzylethylenediamine salts. Pharmaceutically acceptable salts (of basic nitrogen centers) include, but are not limited to inorganic acid salts such as the hydrochloride, hydrobromide, sulfate, phosphate; organic acid salts such as trifluoroacetate and maleate salts; sulfonates such as methanesulfonate, ethanesulfonate, benzenesulfonate, p-toluenesulfonate, camphor sulfonate and naphthalenesulfonate; and amino acid salts such as arginate, gluconate, galacturonate, alaninate, asparginate and glutamate salts (see, for example, Berge, et al. (1977).

The term "first pass metabolism or effect" refers to the amount of drug removed by the liver (& converted to one or more metabolites) during the drug's initial passage through that organ following oral dosing.

Advantages of the Compounds of the Invention

In vitro studies provided herein have demonstrated a direct effect of cancer cells in stimulating megakaryocytopoiesis and furthermore that anagrelide can, despite this stimulatory effect, still markedly inhibit megakaryocytopoiesis. Thereby the "vicious cycle" of cancer cell-platelet interaction is broken offering an entirely new approach to the treatment of cancer.

An advantage of the invention is that for the first time it has been shown that anagrelide, at clinically relevant plasma concentrations, inhibits an observed migratory attraction of circulating cancer cells towards megakaryocytes. Megakaryocytes are normally principally located in bone marrow, and lungs and so reducing any chemotactic response of cancer cells towards these sites should limit such localization and thereby potential for metastasis there. This again offers a radically new approach to the treatment of cancer.

The present invention has the benefit of being broadly applicable to treating a range of cancers of widely different origin since the same platelet mediated mechanism of tumour growth and metastasis development appears to prevail across most cancer types (see list below). Indeed paraneoplastic thrombocytosis is evident in many cancers and is now appreciated to be induced by it. Furthermore the evidence is now compelling across many different cancers that the magnitude of the platelet count determines survival. Thus far, rates of survival have been shown to be related to platelet number for the following cancers:—

Brain,—Brockmann M S et al (2007) Williams M et al (2012)

Oral cavity (including head and neck, nasopharyngeal, oesophageal)—Rachidi S et al (2014), Furlan C et al (2015) Chen Y-P et al (2015). Verma GR et al (2015)

Thyroid cancer—Sun et al (2013)

Breast cancer Lal I et al (2013), Stravodimou A & Voutsadakis I A (2013), Rajkumar A & Szallasi A (2013), Lung cancer—Yu D, et al (2013), Zhang X, & Ran Y (2015)

Stomach cancer—Lv X et al (2010), Li F-X et al (2014), Voutsadakis I A (2014)

Liver cancer—Lee C-H et al (2015), Pang Q et al (2015)

Gall bladder cancer—Wang R T et al (2015),

Pancreatic cancer—Shimada H et al (2004), Suzuki K et al (2004), Chadha AS et al (2015), Wang H et al (2014)

Ovarian, cervical and endometrial cancer—Lee et al (2011), Yuan L & Liu X (2015) Bottsford-Miller KJ et al (2015), Kawano M et al (2015)

Kidney cancer—Gu L et al (2015)

Prostate cancer—Li F et al (2015)

Colorectal cancer—Josa V et al (2015)

Multiple myeloma—Takagi S et al (2015)

Another important advantage of the present invention is that it enables the safer use of the cytoselective, anti-megakaryocytic agent anagrelide to treat cancer in thrombocytotic patients by utilising one of various cardiac-sparing formulations described herein. These formulations minimise the normal first pass generation of the highly cardiostimulant metabolite, 3-hydroxy anagrelide, a compound 40-fold more potent in this respect than the parent drug but with less activity as a platelet lowering entity.

Anagrelide's inherent potency and consequent low oral daily dose of just 1-2 mg, facilitates the development of low loading formulations of this type namely buccal/sublingual tablets, oromucosal sprays, nasal sprays, pulmonary delivery, rectal or iv/im/sc injections.

An additional advantage of these cardiac sparing formulations is that by virtue of their routes of administration namely buccal/sublingual, oromucosal spray, nasal spray, pulmonary delivery, rectal or iv/im/sc injection they minimise the risk of drug loss from the stomach which may result from chemotherapy-induced emesis in cancer patients.

A further advantage of the invention is that when anagrelide, a pharmaceutically acceptable salt, solvate or an active metabolite thereof is combined with another chemotherapeutic it potentially acts synergistically with other administered chemotherapy agents to increase the effectiveness of such cancer treatment. Such enhancement may result in the need for lower doses of said chemotherapies and a reduction in the adverse side-effects seen with such agents, such as nausea, vomiting, diarrhoea as well as unwanted reductions in various cellular components of whole blood. Patient compliance may thereby be improved.

This invention also enables potentially beneficial changes to the doses of anagrelide to be used. By increasing the systemic bioavailability of the drug and minimising exposure to the highly cardiostimulant metabolite and cardiovascular risk, lower doses than those currently employed may beused. Anagrelide's oral bioavailability is normally low due to extensive first pass metabolism which not only produces the cardiostimulant 3-hydroxy anagrelide but also other non-pharmacologically active metabolites such as 2-amino-5,6-dichloro-3,4-dihydroquinazoline (RL603). Estimates of the oral bioavailability of anagrelide indicate this to be less than 50%. See:—http://www.fda.gov/OHRMS/DOCKETS/dailys/04/aug04/081604/04p-0365-cp00001-09-Tab-H-vo1.tpdf. It is envisaged therefore that daily doses of these cardiac sparing formulations could be significantly lower than those currently employed.

Furthermore the expected reduction in the often-seen dose-limiting cardiovascular side-effects of anagrelide could enable the use of higher doses, where required in refractory cases. Reduction in side-effects should also offer the benefit of improved patient compliance with fewer patients likely to cease treatment.

Thus in summary this invention seeks to use anagrelide, a pharmaceutically acceptable salt, solvate or active metabolite thereof in any one of a variety of cardiac-sparing formulations in the prophylaxis and/or treatment of metastatic diseases in cancers of widely varying aetiology in patients who have a significantly poorer prognosis due to paraneoplastic thrombocytosis. This would be effected by reduction in platelet numbers breaking the vicious cycle of platelet-cancer cell interaction as well as through inhibition of cancer cell migration towards bone marrow, and lung located megakaryocytes reducing the likelihood of potentially fatal metastases at these sites.

Selected enteral and non-enteral preparations are employed to avoid the oral first pass formation of the highly cardioactive metabolite, 3-hydroxy anagrelide, and offers a safe & radically new approach to the treatment of cancer of widely different origin.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Pharmaceutical Compositions of the Invention

Anagrelide's inherent high potency as a platelet lowering agent—reflected by the drugs in vitro anti-megakaryocytic 1050 of just 26 nM=7 ng/mL & low dosage of the currently employed formulation (unit dose 0.5 mg) ideally lends itself to "low loadable" routes of administration which allows minimisation of hepatic first pass generation of the highly cardioactive metabolite 3-hydroxy anagrelide (1050 0.7 nM). Established drug delivery methods and formulations are available to facilitate this.

Enteral Formulations

Buccal/Sublingual Delivery

The oral mucosa comprising inner cheek, the sublingual area (under the tongue) the gingival area (the gums) and finally the palatal area (roof of the mouth) offers the potential to deliver some if not all of a medication directly into the systemic circulation so minimising first pass hepatic generation of anagrelide's cardioactive metabolite.

Bucca—Sublingual Tablets.

Sublingual tablets of anagrelide may be of various different designs. One such formulation may be similar to that used with Prefibin®/Subutex® (buprenorphine) sublingual tablets. Typical excipients in such tablets include citric acid, anhydrous lactose monohydrate, mannitol, sodium citrate, sodium stearyl fumarate, pregelatinised starch (maize). The tablet is placed under the tongue until dissolved.

Buccal Spray

A buccal spray formulation may be prepared to any one of several designs. One such design may be similar to Subsys®, a fentanyl oral spray. The drug is dissolved in dehydrated alcohol 63.6%, purified water, propylene glycol, xylitol, and L-menthol. A single actuation delivers a 100 µL spray containing an appropriate dose of the drug. Another oromucusal spray is that used in Sativex®, a tetrahydocannabinol/cannabidiol product. Here the spray device uses a gaseous propellant which is liquid carbon dioxide containing 40 mg ethanol/100 µL spray.

Mucoadhesive buccal tablets Buccal tablets of anagrelide may be made in various ways. An example of this type of formulation is to be found in prochlorperazine buccal tablets (Buccastem®). Here the tablet is placed on the gum under the top lip of either side of the mouth. The mucoadhesive ensures the tablet remains in situ and dissolves over a period of the subsequent 1-2 h. Typical excipients include compressible sugar, povidone K30, xanthan gum, locust bean gum, talc, magnesium stearate and riboflavin sodium phosphate.

Mucoadhesive Buccal Films

Self-dissolving thin films of anagrelide which adhere to the inside of the cheek may be made according to several different designs. One such design may resemble that used for Breakyl® (fentanyl). Breakyl® is a soluble rectangular, flat, flexible buccal film with one side adhering to the inside of the cheek and the other designed to minimise drug release into the saliva and loss of drug by swallowing. Patches of different drug strength are envisaged and would range in size from 0.8 $cm^2$ to 2.4 $cm^2$.

Buccal Lozenges/Lollipop

Again these may be of various designs but in essence are hard sugar lump preparations containing the drug ideally in this case at a pH of ~3 at which the drug is significantly more water soluble than at pH7 (250 µg/mL vs ~1.0 µg/mL). Such lozenges may be mounted on a short plastic stick analogous to that of the Actiq® lollipop formulation of fentanyl. Typical excipients include hydrated dextrates, citric acid, dibasic sodium phosphate, artificial berry flavourings, magnesium stearate, and edible glue (modified food starch and confectioners sugar).

Rectal Formulation.

Rectal administration reduces the extent of first pass metabolism by enabling the drug to be absorbed by the inferior and middle haemorrhoidal veins which drain directly into the systemic blood supply.

Rectal Suppositories.

Suppository formulations frequently utilise meltable wax e.g. Witepsol H14 or 45 or cocoa butter and white wax. An alternate rectal formulation design involves encapsulating a solution of the drug in a suppository-shaped soft gelatin capsule. Once inserted in the rectum the gelatin shell dissolves and releases the drug solution for absorption. A prototypical suppository formulation of anagrelide may be based on that for promethazine suppositories which contain 12.5 mg or 25 mg promethazine HCl with ascorbyl palmitate, silicon dioxide, white wax, and cocoa butter.

Rectal gels of anagelide may be made to various different designs. An anagrelide rectal gel may, for example, resemble that used for diazepam as Diastat Acudial®, a non-sterile diazepam gel provided in a prefilled, unit-dose, with an applicator for direct rectal instillation. Diazepam rectal gel contains drug together with propylene glycol, ethyl alcohol (10%), hydroxypropyl methylcellulose, sodium benzoate, benzyl alcohol (1.5%), benzoic acid and water.

Non Enteral (Parenteral) Formulations

These routes of administration would once again minimise or even avoid altogether hepatic generation of the anagrelide's highly potent cardio-active metabolite. Generic descriptions of the various such formulations are to be readily found in Remington, The Science and Practice of Pharmacy, $22^{nd}$ Edition, 2012.

Nasal Spray

A nasal spray of anagelide may be forrmulated in a manner comparable to that used for desmopressin (Stimate® nasal spray). An aqueous solution/suspension of the drug is contained within a 10 mL plastic reservoir beneath a finger actuated pump. Each actuation delivers 100 µL of spray into each nostril providing the requisite dose of the drug. Alternatively anagrelide may be prepared for nasal delivery in a manner similar to that for midazolam. Typically this uses a concentrated water/propylene glycol drug solution pH 4.0 drawn into a syringe to which is then attached an intranasal mucosal atomization device e.g. LMA® MAD NASAL™. Each spray delivers ~100 µL of solution and in this case two actuations in each nostril gives the requisite amount of the drug. Using this means of administration increased the bioavailablity of midazolam at this dose from ~30% when given orally to 87% (Bjorkman et al 1997).

Pulmonary Delivery

While traditionally associated with local therapy in the treatment of such conditions as bronchial asthma, intrapulmonary drug administration offers a potentially valuable route of systemic delivery. Indeed the inhalation of cigarette smoke or more recently the use of various so-called "vaping" nicotine products present a novel form of systemic delivery. Using a vaping device offers an easy method of formulating a drug for such delivery. For details see "Electronic vaping device and components thereof" in WO 2015131058 A1. Alternatively the traditional propellant driven or dry powder inhaler offers a means of direct delivery into the systemic circulation and avoidance of first pass metabolism. Details of the design of traditional metered dose inhaler can be found in "Metered dose inhaler for albuterol" U.S. Pat. No. 6,131,566 A.

Topical Delivery

Also envisaged within the scope of this invention would be a topical formulation of anagrelide which would be absorbed through the skin and again avoid first pass metabolism. Such formulations may include self-adhesive transdermal patches of either reservoir or matrix types. A transdermal patch formulation of anagrelide may be made in a manner similar to that for buprenorphine (BUTRANS®) or rotigotine (Neupro®)

Injection

Alternative cardio-sparing formulations would be those utilizing the intravenous, intramuscular or subcutaneous routes of administration where the drug may be given either as immediate and sustained release preparations. In the latter case these would embrace dosage forms that release the drug over a predetermined period of time once administered. These would include use of intra-dermal implants or intramuscular injection of depot formulations. For intramuscular depot formulations these could include any one of the various approaches to such delivery such as dissolution controlled, absorption controlled, encapsulation controlled, dissolved in a suitably viscous or oily vehicle. Implants would include any number of device types which are based around the use of Silastic® (silicone elastomers) rods as well as those using other polymeric materials.

Facilitating Improved Aqueous Solubility.

Between pH 4-8 anagrelide's aqueous solubility is only ~1.0 μg/mL. Anagrelide would therefore be classified as a low solubility/high permeability drug under the FDA's Biopharmaceutics Classification System.

Solubility and thereby absorption may be facilitated by use of various penetration enhancers again which are well known in the art. These would include surfactants, both anionic and cationic as well as non-ionic, fatty acids and derivatives including oleic acid and caprylic acid, bile salts, polyols such as propylene glycol (see Dodla & Velmurugan, 2013).

All the aforementioned formulations may benefit from the use of either micronised drug (<100(microns)μm or more ideally <10 μm) or nanoparticulate material (generally <0.1 μm) to increase the surface area and hence rate of dissolution and so facilitate absorption. Preparation of such particle size reduced material is well known to those familiar with the art but is extensively described by Joshi J T (2011) in "A review of micronization techniques" and also in "Drug delivery nanoparticles; formulation and characterization" by Pathak & Thassu (2009).

A further means of increasing the aqueous solubility of anagrelide (and related compounds) would be through the use of reversible complexes with β cyclodextrins. (See Rasheed et al, 2008).

For those formulations of anagrelide where pH adjustment is possible, use of slightly acidic pH's <4 are desirable as this markedly increases the aqueous solubility of the drug. At pH1 for example the aqueous solubility of anagrelide is increased to 236 μg/mL. (see http://www.shirecanada.com/en/documents/AGRYLIN_PM_EN.pdf)

The present invention provides a pharmaceutical composition comprising at least one active pharmaceutical ingredient, or a pharmaceutically acceptable derivative (e.g., a salt or solvate) thereof, and a pharmaceutically acceptable carrier. In particular, the invention provides a pharmaceutical composition comprising a therapeutically effective amount of anagrelide (or an appropriate active metabolite) and a pharmaceutically acceptable carrier.

The drug employed in the present invention may be used in combination with other therapies and/or active agents. Accordingly, the present invention provides a pharmaceutical composition comprising at least one compound useful in the practice of the present invention, or a pharmaceutically acceptable salt or solvate thereof, a second active agent, and, optionally a pharmaceutically acceptable carrier.

When combined in the same formulation it will be appreciated that the two compounds are preferably stable in the presence of, and compatible with each other and the other components of the formulation. When formulated separately they may be provided in any convenient formulation, in such manner as are known for such compounds in the art.

Formulations may be presented for use with the aid of one or more suitable carriers. Acceptable carriers for therapeutic use are well-known in the pharmaceutical art, and are described, for example, in Remington's Pharmaceutical Sciences, 22nd edition 2012. The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

Preservatives, stabilizers, dyes and even flavouring agents may be provided in the pharmaceutical composition. Examples of preservatives include sodium benzoate, ascorbic acid and esters of p-hydroxybenzoic acid. Antioxidants and suspending agents may also be used.

The compounds used in the invention may be milled using known milling procedures such as wet milling to obtain a particle size appropriate for tablet formation and for other formulation types. Finely divided preparations of the compounds may be prepared by other processes known in the art, for example see International Patent Application No. WO 02/00196 (SmithKline Beecham) and would include micronisation as well as the use nanoparticulate material.

The compounds and pharmaceutical compositions of the present invention are intended to be administered either enterally (but only using the proximal (buccal mucosa) and distal ends [rectum] of the GI tract) or parenterally. For enteral use the preparation may comprise a sublingual tablet, mucoadhesive buccal tablet, oromucosal spray, hard lozenge, lollipop lozenge on a stick, suppository, or a rectal gel or suspension. For non-enteral delivery, a nasal spray, pulmonary delivery device, a vaping device or for injection a premix preparation, ovule, solution, suspension, dispersion, gel, or implants/depot formulations. Solid and liquid compositions may be prepared according to methods well-known in the art. Such compositions may also contain one or more pharmaceutically acceptable carriers and excipients which may be in solid or liquid form.

Dispersions can be prepared in a liquid carrier or intermediate, such as glycerin, liquid polyethylene glycols, triacetin oils, and mixtures thereof. The liquid carrier or intermediate can be a solvent or liquid dispersive medium that contains, for example, water, ethanol, a polyol (e.g., glycerol, propylene glycol or the like), vegetable oils, non-toxic glycerine esters and suitable mixtures thereof. Suitable flowability may be maintained administration of a suitable particle size in the case of dispersions, or by the addition of surfactants.

Oromucosal formulations may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

Examples of pharmaceutically acceptable disintegrants for oromucosal compositions useful in the present invention include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and crosslinked polyvinylpyrrolidone.

Examples of pharmaceutically acceptable binders for oromucosal compositions useful herein include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium aluminum silicate, polyethylene glycol or bentonite.

Examples of pharmaceutically acceptable fillers for oromucosal compositions useful herein include, but are not limited to, lactose, anhydrolactose, lactose monohydrate, sucrose, dextrose, mannitol, sorbitol, starch, cellulose (particularly microcrystalline cellulose), dihydro- or anhydrocalcium phosphate, calcium carbonate and calcium sulfate.

Examples of pharmaceutically acceptable lubricants useful in the compositions of the invention include, but are not limited to, magnesium stearate, talc, polyethylene glycol, polymers of ethylene oxide, sodium lauryl sulfate, magnesium lauryl sulfate, sodium oleate, sodium stearyl fumarate, and colloidal silicon dioxide.

Examples of suitable pharmaceutically acceptable odorants for the oromucosal compositions include, but are not limited to, synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oromucosal compositions include, but are not limited to, synthetic and natural dyes such as titanium dioxide, beta-carotene and extracts of grapefruit peel.

Examples of useful pharmaceutically acceptable coatings for oromucosal compositions, to modify the release properties, improve the appearance, and/or mask the taste of the compositions include, but are not limited to, hydroxypropylmethylcellulose, hydroxypropylcellulose and acrylate-methacrylate copolymers.

Suitable examples of pharmaceutically acceptable sweeteners for oromucosal compositions include, but are not limited to, aspartame, saccharin, saccharin sodium, sodium cyclamate, xylitol, mannitol, sorbitol, lactose and sucrose.

Suitable examples of pharmaceutically acceptable buffers useful herein include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants useful herein include, but are not limited to, sodium lauryl sulfate and polysorbates.

Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

Suitable examples of pharmaceutically acceptable stabilizers and antioxidants include, but are not limited to, ethylenediaminetetriacetic acid (EDTA), thiourea, tocopherol and butyl hydroxyanisole.

The pharmaceutical compositions of the invention may contain from 0.01 to 99% weight per volume of the drugs encompassed by the present invention.

Dosages

The doses referred to throughout the specification refer to the amount of the anagrelide free base equivalents or appropriate active metabolite, unless otherwise specified.

Appropriate patients to be treated according to the invention include any human in need of treatment but particularly those cancer patients displaying thrombocytosis. Methods for the diagnosis and clinical evaluation of various cancers, including the severity of such conditions experienced by humans are well known in the art. Thus, it is within the skill of the ordinary practitioner in the art (e.g., a medical doctor/oncologist) to determine if a patient is in need of treatment.

Typically, a physician will determine the actual dosage which will be most suitable for an individual subject with respect to reduction in platelet number. The specific dose level and frequency of dosage for any particular individual may be varied and will depend upon a variety of factors such as route of administration, age, body weight, general health of the individual undergoing therapy, drug combination, the severity of the particular condition (& critically the starting platelet count and rate of change of platelet count in that individual).

The target final platelet count should be in the range $150$-$400 \times 10^3/\mu L$ blood.

Ideally, the platelet count will be reduced to an upper limit of $350 \times 10^3/\mu L$ but above a lower limit of $150 \times 10^3/\mu L$.

More ideally the platelet count will be reduced to an upper limit of $300 \times 10^3/\mu L$ but above a lower limit of $150 \times 10^3/\mu L$.

Most ideally the platelet count will be reduced to an upper limit of $250 \times 10^3/\mu L$ but above a lower limit of $150 \times 10^3/\mu L$.

The cardio-sparing dose formulations herein proposed are different from those of the current commercial formulations of anagrelide and are designed to reduce first pass generation of the cardioactive metabolite and as a consequence adverse cardiovascular effects. Whilst the doses are likely to be lower due to the potential improvements in systemic availability of the drug, the reduction in cardiovascular side effects, which hitherto may have been dose limiting, may enable higher doses to be used when required.

Typically however in the clinical setting it is generally expected that doses of less than half that of the current typical 2-3 mg oral daily dose of anagrelide would be efficacious in reducing platelet count and as a consequence, effective in minimising the risk of cancer progression in thrombocytotic cancer patients. The doses may be adjusted on a daily, weekly or monthly basis depending on the degree of thrombocytosis, as defined by the platelet count, observed.

Typically, anagrelide is likely to be administered twice daily. However the drug may need to be given less frequently or discontinuously depending on the observed platelet count and type of formulation used. The dosing frequency and the possible need for discontinuous dosing will need to be considered depending on the severity of the observed thrombocytosis. Typically, a physician will determine the actual dosage which will be most suitable for an individual subject.

The anagrelide formulations envisaged in this invention may be administered in conjunction with other therapies and/or in combination with other active agents. For example, the drug products encompassed by the present invention may be administered to a patient in combination with other active agents used in the management of the condition. This may include disease modifying drugs such as inhibitors of growth factors or cytokines, chemotherapeutic agents and/or palliative remedies for pain. An active agent to be administered in combination with the drugs encompassed by the present invention may include but not exclusively so, a drug selected from the group comprising alkylating agents, antimetabolites, anti-tumor antibiotics, anti-androgens, anti-oestrogens, topoisomerase inhibitors, mitotic inhibitors, anti angiogenic agents, tyrosine kinase inhibitors, immunotherapies including "check-point" inhibitors corticosteroids and miscellaneous chemotherapeutic agents. Additionally patients may be given anti-aggregatory drugs (anti-platelet agents) such as aspirin, clopidogrel, prasugrel, dipyridamole etc. For pain relief patients may also be given analgesics, both opioid and non-opioid, to control pain In such combination therapies the drugs encompassed by the present invention may be administered prior to, concurrent with, or subsequent to the other therapy and/or active agent. The appropriate doses of these co-medications will be determined by their potency and the severity of the disease.

Where the drug products encompassed by the present invention are administered in conjunction with another active agent, the individual components of such combinations may be administered either sequentially or simultaneously in separate or combined pharmaceutical formulations by any convenient route. When administration is sequential, either the drug products encompassed by the present invention or the second active agent may be administered first. For example, in the case of a combination therapy with another active agent, the drug products encompassed by the present invention may be administered in a sequential manner in a regimen that will provide beneficial effects of the drug combination. When administration is simultaneous, the combination may be administered either in the same or different pharmaceutical composition. For example, a drug encompassed by the present invention and another active agent may be administered in a substantially simultaneous manner, in a fixed ratio of these agents, or in multiple separate dosage forms for each agent.

When the drugs of the present invention are used in combination with another agent active in the methods for treating different cancers, the dose of each compound may differ from that when the compound is used alone. Appropriate doses will be readily appreciated by those of ordinary skill in the art.

EXAMPLES

Example 1

Demonstration of Anagrelide's Inhibitory Effects on Cancer Cell Mediated Megakaryocyte Expansion Experimental Procedures:

Drugs—Anagrelide hydrochloride was purchased from Tocris Bioscience (Bristol, UK). A stock solution was made in DMSO, stored in aliquots at −20° C. and when required diluted in culture medium immediately before experiments.

Cells and drug treatment—Megakaryocytes (MKs) were generated ex-vivo essentially as previously described (Ahluwalia M et al 2010). In brief, to promote terminal megakaryocytic differentiation pre-expanded human umbilical cord blood-derived CD34$^+$ haematopoietic cells were cultured for 7 days in Stemspan™ SFEM II medium (Stem Cell Technologies) supplemented with 1% human umbilical cord blood plasma and 40 ng/ml thrombopoietin (TPO) unless otherwise indicated (MK medium). Where required, anagrelide (1 pM) or an equivalent amount of vehicle was added at the beginning of the differentiation period.

The human ovarian cancer cell line COV362 was grown in Iscove's modified Dulbecco's medium (IMDM) supplemented with 2 mM glutamine and 10% foetal bovine serum (FBS). Cell cultures were maintained at 37° C. in a humidified incubator under 5% CO2/95% air.

Co-culture experiments—Co-culture of COV362 cells (COVs) and developing MKs was carried out in a modified Boyden Chamber (BD Falcon, BD Biosciences, Oxford, UK) consisting of a cup-shaped cell culture insert resting inside the well of a 24-well companion plate, with the bottom of the insert made of a permeable microporous polyethylene terephthalate (PET) membrane having a pore size of 0.4 µm.

In experiments examining the effects of COVs on MK development, COVs were seeded in the companion plate at various cells densities and grown for 4 days prior to mounting the inserts. Then, the medium in the companion plate was removed and replaced with fresh MK medium. Immediately thereafter the pre-expanded haematopoietic cells were seeded in the insert. After seven days of co-culture the cells growing in the inserts were harvested for analysis of MK development.

Analysis of megakaryocyte development—Cell density was determined using a Casy TT Cell counter (Innovatis, Germany) set with a lower cut-off limit of ~7.5 µm. MK-specific antigen expression was monitored by flow cytometry using a fluorescein isothiocyanate-conjugated anti-CD61 antibody (clone Y2/51, Dako, Ely, UK) as previously described (Wang G et al 2005). The number of MKs was calculated by multiplying the total number of cells in the culture by the fraction of CD61 positive cells.

Results (See FIG. 1)—In the absence of COVs, thrombopoietin driven MK expansion was clearly demonstrated which in the presence of anagrelide (1 µM) was, as expected from previously reported data, inhibited by ~50%. In the presence of COVs (seeded at 1000cells/mL) MK numbers were increased by a remarkable 148% and by nearly 160% with a greater number of COVs (seeded at 3000 cells/mL). Addition of anagrelide (1 µM) substantially reduced the increase in MK expansion seen in the presence of COVs. In the case of 1000cells/mL the stimulatory effects of COVs was completely abolished while with 3000cells/mL the expected increase was more than halved.

Discussion—These results conclusively demonstrate a direct effect of cancer cells in stimulating megakaryocyte expansion and thereby platelet production. In the present study the pore size of the membrane separating the OVCs and MKs precluded physical movement of the former and thus the effect witnessed must have been due to a COV chemokine release of some sort. Platelets via their growth factors are known to play a key role in cancer development and progression. Previously the role of cancer cells in expansion of megakaryocytes had generally been considered to be an indirect process via cytokine (interleukins, particularly IL-6 see Davis et al 2014) release from cancer cells and subsequent stimulation of the liver to produce thrombopoietin which in turn accelerates megakaryocyte/platelet production, further fuelling cancer cell growth in what has been described as a vicious cycle or pathogenic loop. The current study has shown cancer cell secretions to be capable of directly stimulating megakaryocyte expansion. Importantly this study has demonstrated that even in the presence of such stimulatory effects of cancer cells, anagrelide is still able to profoundly inhibit this effect. This newly discovered property of anagrelide affords the opportunity to reduce MK expansion in response to cancer cells and thereby the progression and development of the disease.

Example 2

Demonstration of Anagrelide's Inhibitory Effects on Cancer Cell to Megakaryocyte Migration Transmigration assay—Transmigration of human ovarian cancer cells, COV362 cells (COVs), was examined in a well established model of cancer cell migration (Hart et al 2005) and Kramer et al 2013) which employed the modified Boyden chamber described above but using inserts with a larger 8μm pore PET membrane. This pore size enabled cancer cells to move through to the under section of the chamber in response to any attract properties displayed by megakaryocytes beneath. In this case pre-expanded haematopoietic cells were grown for 7 days in MK medium in the wells of the companion plate prior to placement of the inserts. Inserts were then positioned inside these MK-containing wells or in parallel wells filled with and equivalent volume of MK medium alone. A suspension of 0.35 mL COVs cells made in plasma-free MK medium at a density of $2.86 \times 10^5$ cells/ml was then loaded onto the inserts and allowed to trans-migrate through the PET membrane for up to 24 h at 37° C. in a tissue culture incubator. At various time points the transmigration assay was terminated by removing the insert from the well of the companion plate and aspirating its contents. After washing the inserts with phosphate-buffered saline (PBS) non-migrating cells attached to the upper side of the PET membrane were scraped off with cotton swabs soaked in PBS. Migrated cells on the underside of the PET membrane were stained with 0.5% crystal violet in 25% methanol. Bright field digital photomicrographs were taken in five random fields at 100× magnification and the average number of cells per field was determined by manual counting.

Figure 2:
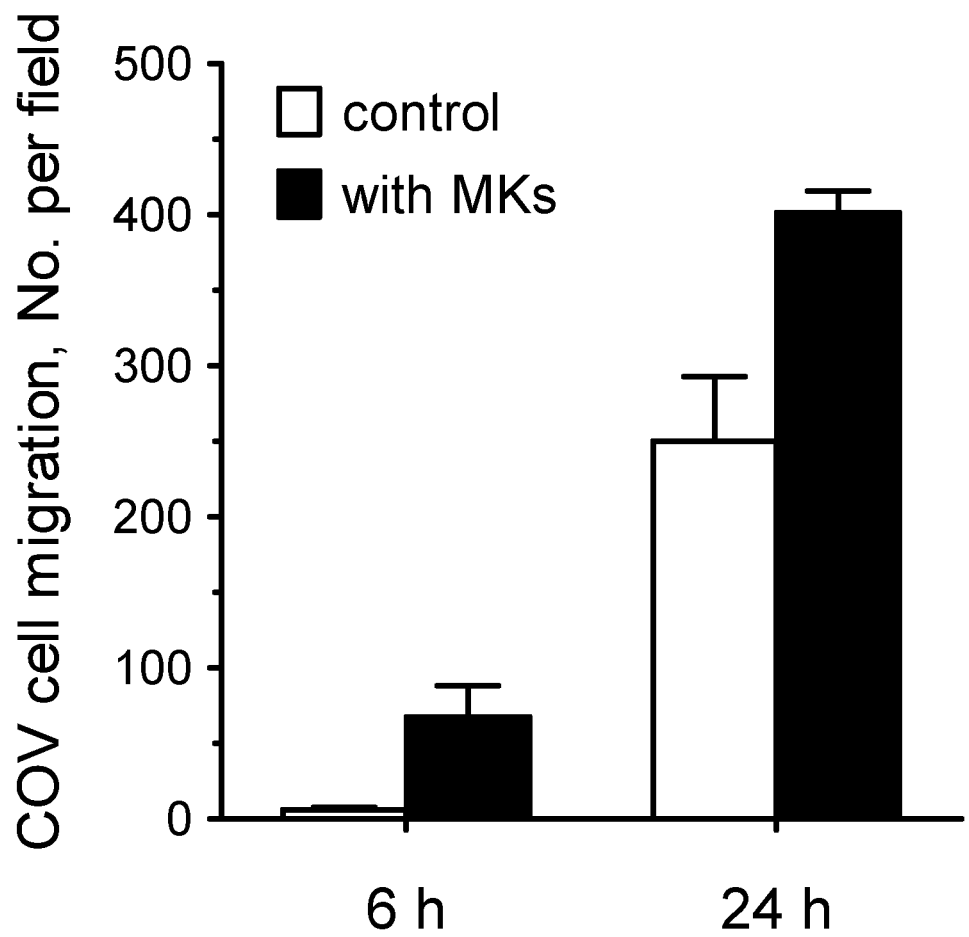
FIG. 2. Megakaryocytes enhance the migration of ovarian cancer cells. COV362 cells were loaded onto a Boyden Chamber and their transmigration towards seven day-MK cultures or to an equivalent amount of MK medium (control) was determined at the indicated times as described under Experimental Procedures. Results represent the number of migrated COV362 cells per photomicrographic field (mean±SEM of 5-10 fields per condition).
Figure 3:
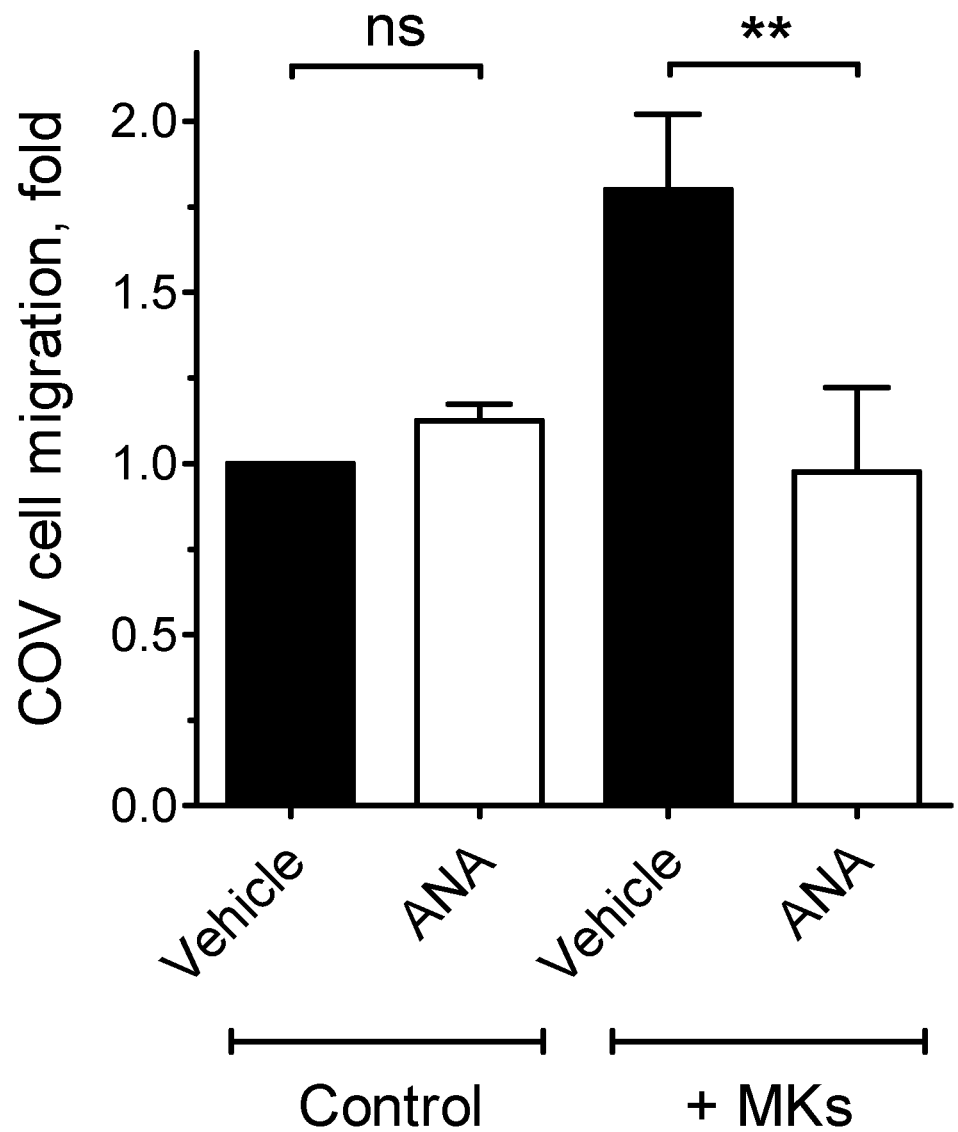
FIG. 3. Anagrelide inhibits megakaryocyte enhancement of ovarian cancer cell migration. COV362 cells were loaded onto a Boyden Chamber and their transmigration towards seven day-MK cultures grown in the absence or presence of anagrelide (1 µM) or towards an equivalent amount of MK medium (control) was determined after an overnight incubation, as described under Experimental Procedures. Results (mean±SEM of 4 experiments) are expressed relative to the number of COV362 cells that migrated towards growth medium alone. **, $P<0.01$ by ANOVA with Bonferroni's post hoc test; ns, non-significant.
Figure 4:
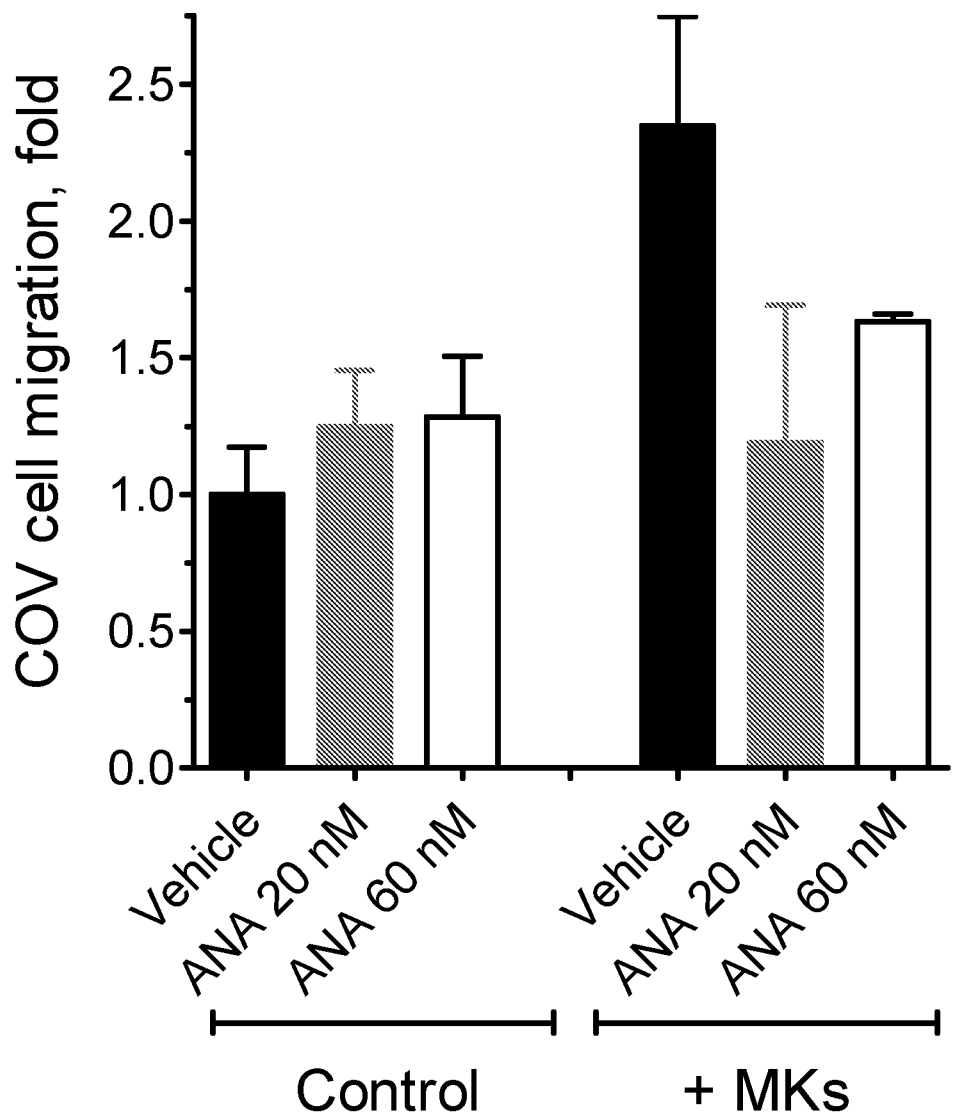
FIG. 4. Anagrelide inhibits megakaryocyte enhancement of ovarian cancer cell migration at clinically relevant concentrations. COV362 cells were loaded onto a Boyden Chamber and their transmigration towards seven day-MK cultures grown in the absence or presence of the indicated concentrations of anagrelide or towards an equivalent amount of MK medium (control) was determined after 16 h, as described under Experimental Procedures. Results (mean±SEM of 2 replicate wells) are expressed relative to the number of COV362 cells that migrated towards growth medium alone.

Results (See FIGS. 2, 3 & 4)—Extensive migration of COVs toward the MK cultures contained within the lower section of the modified Boyden chamber was shown in the current study demonstrating a chemoattractant characteristic of MKs for COVs in this model. In the absence of MKs, migration of COVs was very much slower reflecting very modest attractant properties of the plasma-containing medium added to the lower section of the chamber in the control incubates. This attractant behaviour of MKs with respect to COVs was clearly demonstrated to be time dependent (FIG. 2). Strikingly addition of MK cultures grown in the presence of anagrelide (1 μM) was found to have no attractant properties for COVs (FIG. 3). The loss of attractant properties was also manifest when MKs were grown at clinically relevant concentrations of the drug (FIG. 4).

Discussion—As a model for the behaviour of cancer cells migrating to repositories of megakaryocytes in bone, & lung—and thereby the potential to establish metastases at these locations—the data generated in this study provide invaluable insight into the likely beneficial effects of anagrelide in inhibiting this process. The first cells encountered upon entry of cancer cells into bone marrow are megakaryocytes and data from the current study have conclusively—and surprisingly—shown positive attractant behaviour of MKs for ovarian cancer cells. The nature of this binding interaction is likely complex and to involve multiple processes which may be similar to those reported for tumour cell-platelet interactions (Erpenbeck & Schon 2010). Furthermore it is this attractant property of megakaryocytes for cancer cells that is likely to play a key role in the establishment of metastatic disease. In this context anagelide offers the great potential to profoundly alter the course of metastatic disease.

Example 3

Demonstration of Anagrelide's Ability to Reduce Platelet Derived Cancer Cell Growth Factors Platelet Factor 4 and Vascular Endothelial Growth Factor (after Cacciola et al 2004

Thirteen patients (eight men and five women mean age of 53 years) with essential thrombocythemia-ET (mean duration of disease 4 years) were recruited into this study. Four patients received hydroxyurea (HU)1.25 g/day, three patients interferon alpha (IFN-α) $1.5 \times 10^6$ units/day, and six anagrelide (A) 1.5 mg/day. Ten healthy subjects served as controls.

PF4 and VEGF were measured by an enzyme linked immunosorbent assay (Boehringer-Mannheim, Germany). Platelets were determined on a Sysmex XE-213000 (Dasit, Italy).

Before treatment all patients had a high platelet count $1045+/-207 \times 10^3/\mu L$ and higher PF4 and VEGF (levels (137+/−63 IU/mL and 1.5+/−0.7 pg/mL than the controls 2.1+/−1.5 IU/mL and 0.2+/−0.08 pg/mL.

After treatment patients had a mean platelet count of $400+/-62 \times 10^3/\mu L$. Neither HU nor IFα brought PF4 and VEGF down and interestingly only anagrelide treatment reduced the PF4 and VEGF levels to normal suggesting that only anagrelide induces normalization of platelet function.

While this study was conducted with respect to investigating the effects of these drugs in ET patients, the now appreciated role of both of these growth factors in cancer cell growth and tumour angiogenesis puts the significance of these data in a new context. Of the most commonly used treatments for platelet lowering (in ET) only anagrelide is likely to lower circulating plasma levels of these important two growth factors and hence have a positive therapeutic effect on cancer cell and tumour development.

Example 4

Estimation of Anagrelide Doses Required to Effect Platelet Reduction but Minimise Cardiovascular Risk The proposed dosage of the cardio-sparing formulations herein described may be different from those of the current commercial formulations as the result of improvement in systemic availability & reduction in the adverse cardiovascular effects. Whilst doses are likely to be lower due to potential improvements in systemic availability of the drug, the reduction in cardiovascular side effects, which hitherto been may have dose-limiting, may enable higher doses to be used in refractory cases. The following determination offers useful insight.

The highly undesirable cardiovascular effects of anagrelide are due to first pass formation of 3-hydroxy anagrelide and the profound difference in respective IC50 values of this metabolite compared to that for drug with respect to inhibition of PDE III—(the mechanism by which these effects are brought about). For the metabolite this is just 0.7 nM (0.2 ng/mL) but for the drug 32 nM (8.2 ng/mL).

After a typical 1 mg clinical dose peak plasma levels of the metabolite are 29 nM (~8 ng/mL) some 40-fold greater than its in vitro PDE III inhibitory IC50. Even allowing for any non specific tissue binding in vivo this is still likely to greatly exceed the IC50. By contrast anagrelide peak plasma levels are just 16 nM (~4 ng/mL) only 50% of its in vitro PDEIII inhibitory IC50. Given the likely non specific tissue binding in vivo this is potentially unlikely to have any great effect in vivo. Thus as is self-evident, this metabolite is likely to be the overwhelming contributor to the cardiovascular effects of the drug.

Using any one of the proposed cardiac sparing formulations is likely to substantially increase the systemic availability of anagrelide and so dramatically reduce the normally first pass generated cardiotoxic metabolite. In the best case scenario the bioavailability of anagrelide after iv dosing is, by definition 100% with no first pass generation this metabolite. With the other formulation strategies proposed herein, historical precedent predicts likely increases in anagrelide bioavailabilities to >75% and hence a dramatic reduction in first pass generated metabolite. When taking into account the magnitude of the cardiovascular potency difference between this metabolite and the parent drug such a reduction in first metabolite generation becomes much more profound and the burden of CV effects much less.

This calculation illustrates the potential value of lowering exposure to the metabolite to minimise the unwanted cardiovascular effects.

Example 5

Preparation of Anagrelide Buccal Tablets

Anagrelide buccal tablets may be prepared in various different ways. One approach would be in manner similar to that used for the transmucosal delivery of glibenclamide, another BCS class II compound, of similar water solubility and given at a similar dose level (Sarfarez et al 2011). Anagrelide mucoadhesive buccal tablets may be made by the direct compression method using bioadhesive polymers such as Carbopol 934P, HPMC K4M and NaCMC. A preferred anagrelide buccal tablet design has the following composition:—micronised(<10 μm) anagrelide loading 0.25-2.5 mg, Carbopol-934P 46 mg, HPMC 46 mg, mannitol 94 mg, magnesium stearate 2 mg, talc 2 mg. This preparation would be expected to have a bioadhesive strength of the order of ~3.5 g. The overall likely surface pH of ~7 presents minimal risk of mucosal damage while such a bioadhesive strength value indicates good adhesiveness to the buccal mucosa.

Example 6

Preparation of Anagrelide Buccal Thin Film Slow Release Formulation

Anagrelide buccal thin film formulations may be prepared in several different ways. One formulation strategy may be similar to those used for the transmucosal delivery of glibenclamide, another BCS class II compound which is given at a similar dose level (Bahri-Najafi R et al 2014). Self-dissolving thin film buccal formulations have the advantage of better patient compliance due to the ease of administration. Mucoadhesive buccal films of micronised anagrelide may be prepared using hydroxypropyl methyl cellulose (HPMC) K4M, K15M or Eudragit RL100 polymers and propylene glycol as plasticizer and co-solvent. Films are prepared using the solvent casting method. Those using Eudragit RL100 are the most preferred as they tend to be transparent, uniform, flexible and avoid bubble enclosures. The optimal composition of such a formulation would contain 0.25-2.5 mg drug and ~100 mg of the Eudragit polymer with a typical film thickness of ~250 μm. The surface pH is likely to be in the range 6.2-6.6. and the bioadhesion force of the order of ~5N. The drug release profile is likely to show >90% being released over 6 h

Example 7

Preparation of Alternate Anagrelide Buccal Thin Film Slow Release Preparation An alternate design for a mucoadhesive buccal thin film of anagrelide could be made in a manner similar to that for BUNAVAIL® This buccal film of buprenorphine and naloxone is a citrus flavoured oral transmucosal form, intended for application to the buccal mucosa. Each dose unit is a yellow rectangular film, with ink marking on the mucoadhesive side. The film adheres upon contact with the moist buccal mucosa and gradually dissolves releasing the drug for local absorption. Each film also contains carboxymethylcellulose sodium, citric acid, citrus blend flavour, dibasic sodium phosphate, blue ink, hydroxyethyl cellulose, hydroxypropyl cellulose, methylparaben, monobasic sodium phosphate, polycarbophil, propylene glycol, propylparaben, yellow iron oxide, sodium benzoate, sodium hydroxide, sodium saccharin, vitamin E acetate, and purified water. The blue ink contains FD&C blue #1, ethanol, purified shellac, acetone, ammonium hydroxide and water. A comparable formulation of anagrelide could be prepared available in various strengths, for example 0.1 mg anagelide in a 2.2 cm$^2$ film & 0.25 mg in a 4.4 cm$^2$ film. Intimate details of this method of preparation can be found in patent number U.S. Pat. No. 8,475,832 B2 "Sublingual and buccal film compositions".

Example 8

Preparation of an Angrelide Buccal Lozenge/Lollipop

Anagrelide buccal lozenge/lollipop may be formulated in a number of different ways. One approach would be comparable to that used for fentanyl lozenges/lollipop (Actiq), a solid sugar-lump formulation of fentanyl citrate supported on a short plastic stick. When sucked this slowly dissolves in the mouth over a 15 minute period resulting in efficient transmucosal absorption of the drug. In essence such lozenge formulations comprise sugar (dextrose such as Cerelose 2043), a binding agent corn-starch (pre-gelatinized food grade starch) and micronized drug (particle size 1-5 μM). Concentrations of drug in the lozenge may range from 0.25-2.5 mg. Additionally colourings and flavourings such as lemon, pineapple or raspberry may be added along with buffer salts disodium hydrogen phosphate and citric acid to adjust the pH. To maximise the aqueous solubility of anagrelide acidic pH's are preferred, ideally pH3. Finally a plastic stick is secured into a groove created during the lozenge moulding process. Details of the process for the preparation of fentanyl lozenge lollipops can be found in patent number US20070104763 A1. "Composition of fentanyl citrate oral solid dosage form excipient and binding material therefore and methods of making".

Example 9

Preparation of an Oromucosal Spray of Anagrelide

An oromucosal spray is another method of delivery designed to exploit absorption of the drug within the oral cavity. Formulation of anagrelide may be effected in a manner similar to that for Sativex. This comprises a Type I (Ph.Eur.) amber plastic coated glass spray container (10 mL) fitted with a metering pump possessing a polypropylene dip tube and elastomer neck covered with a polyethylene cap. The metering pump delivers 100 microlitre per spray from the reservoir with a volume of 5.5 ml. Micronised anagrelide may be dissolved/suspended in a co-solvent mixture of citric acid buffer propylene glycol and ethanol at the requisite concentration. The pump action spray may be designed to deliver drug amounts between 100-500 μg/100 μL spray. Details of the method used for preparation of Sativex can be found in Patent No. EP 1542657 "Cannabinoid Liquid Formulations for Mucosal Administration".

Example 10

Preparation of a Nasal Spray of Anagrelide

A nasal spray of anagrelide may be forrmulated in a number of different ways. One such would be in a manner analogous to that used for desmopressin (Stimate® nasal spray). For anagrelide an aqueous solution/suspension of the drug would be contained within a 10 mL plastic reservoir attached to a finger actuated pump. This would contain a solution/suspension of micronized anagrelide (1-5 μM particle size) in saline adjusted to pH 3.5 with hydrochloric acid. Alternatively citric acid and disodium phosphate dihydrate may be used as a buffer. Chlorobutanol 0.5% v/v or 0.01% benzalkonium chloride w/v can be used as preservatives. When inserted into the nostril and actuated each spray (100 μL) would deliver between 100-500 μg of drug. Details of the process for preparation of desmopressin nasal spray may be found in U.S. Pat. No. 5,498,598 "A composition for nasal administration of desmopressin" An alternate approach to formulation of a nasal spray of anagrelide is that given for sumitriptan in WO20111036521 A2 "Formulations comprising triptan compounds".

Example 11

Preparation of Pulmonary Inhaler of Anagelide

A dry powder inhaler of anagrelide similar in design to that used for delivery of salbutamol may be employed in which each actuation delivers 100-500 μg of the micronized drug into the lungs upon oral inhalation. The device comprises a small aluminium pressurised canister fitted with a metering valve. The propellant may be a chloroflouro carbon or the newer replacement e.g. 1,1,1,2-tetrafluoroethane. When inserted into a standard plastic actuator which has a plastic mouthpiece each depression of the valve provides a dose of between 100-500 μg of the drug as a "suspension" in lactose. Details of the formulation and preparation of salbutamol using the newer propellant can be found in US 20140286877 A1 "Compositions comprising salbutamol sulphate".

Example 12

Preparation of a Rectal Suppository Formulation of Anagrelide

Anagrelide may be formulated as a suppository by a method analogous to that used for the delivery of diazepam. This comprises preparing 1.3 mL suppositories containing 100-1000 μg anagrelide dissolved/suspended in a base comprising propylene glycol 5 mL, silica gel 2.5 g and Medusca polypeg suppository base. Further details may be found at:—http://www. medisca.net/pdf/sample/F%20001%20603v2%20Diazepam%205%mg%20Rectal%20Suppositories%201.3%20mL.pdf.

Example 13

Preparation of a Rectal Gel Formulation of Anagrelide

A rectal gel of anagrelide may be made in a manner similar to that used for the preparation of diazepam rectal gel (Dabbagh M A et al 2007). In essence this is a rectal hydrogel product comprising drug substance with suitable co-solvents and preservative. Preparation of the base (HPMC) gel may be made by heating two thirds of the required volume of water to 80° C. and then adding an amount of HPMC to give a final formulation concn of ~6%. The remaining quantity of cold water is then added. The required amount of anagrelide drug substance is then mixed with citric acid buffer pH 3.5 (forming 5% v/v final mix) and propylene glycol (forming 50% v/v final mix)+ethanol (forming 2% v/v final mix) as co-solvent. To this is added the preservative benzyl alcohol (2% v/v final mix) & finally the required amount of gel base is added comprising 23% final mix). The prepared formulation may be aliquoted into 3 mL syringes ready for delivery. Amounts to be delivered would be in the range 100-1000 μg anagrelide per instillation.

Example 14

Preparation of Anagrelide Intramuscular Depot Extended-Release Polymeric Microspheres Formulation For depot formulations of anagrelide, preparations similar to those of risperidone, (RISPERDAL® CONSTA®), another BCS Class II compound with a very similar low water solubility, may be used. Such long-acting injection formulations comprise extended-release polymeric microspheres and associated diluent. In the case of RISPERDAL®, the drug is micro-encapsulated in 7525 polylactide-co-glycolide (PLG). The diluent for parenteral use is a clear, colourless solution and includes polysorbate 20, sodium carboxymethyl cellulose, disodium hydrogen phosphate dihydrate, citric acid anhydrous, sodium chloride, sodium hydroxide, and water for injection. The microspheres are suspended in the diluent prior to injection. Formulations of anagrelide may be made in a comparable manner to achieve sustained intramuscular release. Doses for such drug depot formulations may range from 1-10 mg.

Example 15

Preparation of an Alternative Anagrelide Intramuscular Extended Release Depot Formulation Alternatively an anagelide formulation for intramuscular injection may be prepared in a manner similar to the sustained release depot formulation of yet another BCS Class II drug, paliperidone, INVEGA® SUSTENNA® This is presented as a sterile aqueous extended-release suspension in a vehicle comprising polysorbate 20, polyethylene glycol 4000, citric acid monohydrate, disodium hydrogen phosphate anhydrous, sodium dihydrogen phosphate monohydrate, sodium hydroxide, and water for injection. Again a formulation of anagrelide may be made in a comparable to achieve sustained intramuscular release. Doses for such drug depot formulations of anagrelide may range from 1-10 mg.

Example 16

Preparation of a Dermal Implant of Anagrelide

Anagrelide may be prepared as an implant in a manner similar to that for ivermectin, yet another BCS class II drug. The preparation of this latter drug has been described by Maeda et al (2003). Such implants comprise a cylindrical silicone construction with an inner core containing the active and additives such as sodium desoxycholate and sucrose in a silicone matrix. Because water cannot penetrate the silicone outer cover it gains entry through the cross sectional end and causes dissolution of the active ingredient. The dissolved active is then free to diffuse and is released through channels formed in the inner core created as a result of dissolution of the active. Such drug release provides a pseudo zero order profile. The advantage of such implanted drug delivery systems is that they are easily surgically inserted and can be readily removed as and when required. Doses for such drug depot formulations of anagrelide may range from 1-10 mg.

REFERENCES

ASH—55th Annual Meeting New Orleans December 2013. "Platelets & Cancer".
Ahluwalia M, Donovan H, Singh N, Butcher L, Erusalimsky J D (2010) Anagrelide represses GATA-1 and FOG-1 expression without interfering with thrombopoietin receptor signal transduction. J Thromb Haemost, 8, 2252-61.
Ambrus J L, Ambrus C M, Gastpar H. (1986) Effect of imidazoquinolinones on tumor cells in the circulation. J Med. 17, 219-25.
Amo L, Tamayo-Orbegozo E, Maruri N, Eguizabal C, Zenarruzabeitia O, Riñón M, Arrieta A, Santos S, Monge J, Vesga M A, Borrego F, Larrucea S (2014) Involvement of platelet-tumor cell interaction in immune evasion. Potential role of podocalyxin-like protein 1. Front Oncol. 4, 1-7.
Andersen, C L, Siersna V, Hasselbalch H C, Bjerrum O W, Felding P, Lind B, Palmblad J, Olivarious NDF. Prediagnostic thrombocytosis increases the risk of advanced gynecological cancer and increase mortality independently of cancer stage—a population-based study. ASH, 56th Annual Meeting, San Francisco, December 2014, Abstract 2791.
Bahri-Najafi R, Tavakoli N, Senemar M, Peikanpour M (2014) Preparation and pharmaceutical evaluation of glibenclamide slow release mucoadhesive buccal film. Research in Pharmaceutical Sciences 9, 213-223.
Bakewell S J, Nestor P, Prasad S, Tomasson M H, Dowland N, Mehrotra M, Scarborough R, Kanter J, Abe K, Phillips D, Weilbaecher K N. (2003) Platelet and osteoclast beta3 integrins are critical for bone metastasis. Proc Natl Acad Sci; 100, 14205-10.
Bambace N M, Holmes C E (2011). The platelet contribution to cancer progression. J Thromb. Haemost. 9, 237-49.
Battinelli, E M, Kulenthirarajan R Italiano J E Johnson K (2014). Tamoxifen directly disrupts platelet angiogenic potential and inhibits platelet-mediated metastasis Blood: 124, 4169
Berge S M, Bighley L D, Monkhouse D C. (1977). Pharmaceutical salts J Pharm Sci. 66, 1-19.
Birgegård G, Björkholm M, Kutti J, Lärfars G, Löfvenberg E, Markevärn B, Merup M, Palmblad J, Mauritzson N, Westin J, Samuelsson J. (2004) Adverse effects and benefits of two years of anagrelide treatment for thrombocythemia in chronic myeloproliferative disorders. Haematologica. 89, 520-7.
Björkman S, Rigemar G, Idvall J. (1997) Pharmacokinetics of midazolam given as an intranasal spray to adult surgical patients. Br J Anaesth. 79, 575-80.
Borsig L (2008) The role of platelet activation in tumor metastasis. Expert Rev Anticancer Ther. 8, 1247-55.
Bosetti C, Rosato V, Gallus S, La Vecchia C (2012). Aspirin and urologic cancer risk: an update. Nat Rev Urol. 9, 102-10.
Bottsford-Miller J, Choi H J, Dalton H J, Stone R L, Cho M S, Haemmerle M, Nick A M, Pradeep S, Zand B, Previs R A, Pecot C V, Crane E K, Hu W, Lutgendorf S K, Afshar-Kharghan V, Sood A K. (2015) Differential platelet levels affect response to taxane-based therapy in ovarian cancer. Clin Cancer Res. 21, 602-10.
Boucharaba A, Serre C M, Gres S, Saulnier-Blache J S, Bordet J C, Guglielmi J, Clézardin P, Peyruchaud O (2004). Platelet-derived lysophosphatidic acid supports the progression of osteolytic bone metastases in breast cancer. J Clin Invest. 114 1714-25.
Brockmann M A, Giese A, Mueller K, Kaba F J, Lohr F, Weiss C, Gottschalk S, Nolte I, Leppert J, Tuettenberg J, Groden C (2007). Preoperative thrombocytosis predicts poor survival in patients with glioblastoma. Neuro Oncol. 9, 35-42.
Buergy D, Wenz F, Groden C, Brockmann M A. (2012) Tumor-platelet interaction in solid tumors. Int J Cancer. 130, 2747-60.
Cacciola R R, Francesco E D, Giustolisi R, Cacciola E. (2004) Effects of anagrelide on platelet factor 4 and vascular endothelial growth factor levels in patients with essential thrombocythemia. Br J Haematol. 126, 885-6.

Chadha A S, Kocak-Uzel E, Das P, Minsky B D, Delclos M E, Mahmood U, Guha S, Ahmad M, Varadhachary G R, Javle M, Katz M H, Fleming J B, Wolff R A, Crane C H, Krishnan S. (2015) Paraneoplastic thrombocytosis independently predicts poor prognosis in patients with locally advanced pancreatic cancer. Acta Oncol. 54, 971-8.

Chen Y P, Chen C, Mai Z Y, Gao J, Shen L J, Zhao B C, Chen M K, Chen G, Yan F, Huang T Y, Xia Y F (2015) Pretreatment platelet count as a predictor for survival and distant metastasis in nasopharyngeal carcinoma patients. Oncol Lett. 9 1458-1466.

Chen Y G, Lin C S, Shen C H, Chian C F (2012) Platelet-lowering therapy with anagrelide as an adjuvant therapy for treatment of primary pulmonary neoplasm-associated extreme thrombocytosis. Jpn J. Clin. Oncol. 42, 761-3.

Cho M S, Vasquez H G, Stone R, Zand B, Kroll M H, Sood A K, Afshar-Kharghan V (2012). Platelets increase the proliferation of ovarian cancer cells. Blood. 120, 4869-72.

Dabbagh, M A, Ameri, A, Honarmand M (2007) Preparation of diazepam rectal gel using cellulose polymers. Jundishapur Journal of Natural Pharmaceutical Products 2, 34-44

Davis A N, Afshar-Kharghan V, Sood A K. (2014) Platelet effects on ovarian cancer. Semin Oncol. 41, 378-84.

Demers M, Ho-Tin-Noe B, Schatzberg D, Yang J D1 Wagner D D (2011) Increased efficacy of breast cancer chemotherapy in thrombocytopenic mice Cancer Res. 71, 1540-9.

Dodla S, Velmurugan S., (2013) Buccal penetration enhancers—an overview. Journal of Pharmaceutical and Clinical Research. 6, 39-47.

Erpenbeck L, Schon M P (2010) Deadly allies: the fatal interplay between platelets and metastasizing cancer cells. Blood. 115, 3427-36.

Fiuza M (2012) Cardiotoxicity of Oncologic Treatments ISBN 978-953-51-0273-1 Publisher: InTech.

Folkman J (1971) Tumor angiogenesis: therapeutic implications. N. Engl. J Med. 285, 1182-6.

Furlan C, Steffan A, Polesel J, Trovo M, Gobitti C, Vaccher E, Serraino D, Barzan L, Franchin G (2015) Lower platelet counts and antiplatelet therapy independently predict better outcomes in patients with head and neck squamous cell carcinoma: a retrospective analysis. Biomark Res. 3, 25.

Gay L J, & Felding-Habermann B (2011). Contribution of platelets to tumour metastasis. Nat Rev Cancer. 11,123-34.

Gu L, Li H, Gao Y, Ma X, Chen L, Li X, Zhang Y, Fan Y, Zhang X. (2015) The association of platelet count with clinicopathological significance and prognosis in renal cell carcinoma: a systematic review and meta-analysis. PLoS One. 10, 1-12.

Gupta G P, Massague J. (2004) Platelets and metastasis revisited: a novel fatty link. J Clin Invest. 114, 1691-3.

Guo T, Krzystanek M, Szellas Z, Szallas A (2014) Thrombocytosis portends adverse prognostic significance in patients with stage II colorectal carcinoma. F1000Research 3, 180-183.

Gaorav P. Gupta and Joan Massague (2004) Platelets and metastasis revisited: a novel fatty link. J Clin Invest. 114, 1691-1693.

Hale K L (2012) Research explores link between thrombocytosis and cancer. Oncolog. 57, 11-12.

Harrison C N, Bareford D, Butt Net al (2010) Guideline for investigation and management of adults and children presenting with thrombocytosis. Brit. J Haematol. 149, 352-275.

Hart C A, Brown M, Bagley S, Sharrard M, Clarke N W. (2005) Invasive characteristics of human prostatic epithelial cells: understanding the metastatic process. Br J Cancer 92, 503-12.

Hong Y, Wang G, Del Arroyo A G, Hernandez J, Skene C, Erusalimsky J D (2006). Comparison between anagrelide and hydroxycarbamide in their activities against haematopoietic progenitor cell growth and differentiation: selectivity of anagrelide for the megakaryocytic lineage Leukemia. 20, 1117-22.

Ho-Tin Noe B, Goerge T & Wagner D D (2009) Platelets: Guardian of tumour vasculature. Cancer Res. 69, 5623-69.

Hwang S-J, Chyuan J, Ki C-P et al (2004) Thrombocytosis: a pareneoplastic syndrome in patients with heptocellular carcinoma. World J Gastroenterol. 10 (17) 2472-2477.

Jackson W, Mastro A M, Sosnoski D M (2015) Thrombopoietin and megakaryocytes in breast cancer metastasis to bone. Proceedings of the 106th Annual Meeting of the American Association of Cancer Research Apr. 18-22, 2014 Philadelphia.

James C W (2000), Anagrelide-induced cardiomyopathy Pharmacotherapy. 20, 1224-7.

Johnson K E, Machlus K R, El-Husayni S, Kulenthirarajan R, Forward J A, Italiano J E, Battinelli E M. (2015) Platelets promote breast cancer metastasis by reprogramming tumor cell to produce IL-8. ASH 57th Annual Meeting, Orlando, Fla. Dec. 5-8, 2015.

Josa V, Krzystanek M, Eklund A C, Salamon F, Zarand A, Szallasi Z, Baranyai Z. (2015) Relationship of postoperative thrombocytosis and survival of patients with colorectal cancer. Int. J. Surg. 18, 1-6.

Joshi J T (2011) A review of micronization techniques. J. Pharmaceut. Sci. & Technol. 3, 651-681.

Jurgens D, Moreno-Aspitia A, Tefferi A (2004). Anagrelide-associated cardiomyopathy in polycythemia vera and essential thrombocythemia. Haematologica 89, 1394-1395.

Kacena M A, Gundberg C M, Horowitz M C. (2006) A reciprocal regulatory interaction between megakaryocytes, bone cells, and hematopoietic stem cells. Bone. 39, 978-84.

Kawano M, Mabuchi S, Matsumoto Y, Sasano T, Takahashi R, Kuroda H, Kozasa K, Isohashi F, Ogawa K, Kimura T (2015). Prognostic significance of pretreatment thrombocytosis in cervical cancer patients treated with definitive radiotherapy. Int J Gynecol Cancer. 25 1656-62.

Kisucka J Butterfield C E, Duda DG et al (2006) Platelets and platelet adhesion support angiogenesis while preventing excessive haemorrhage. Proc Natl. Acad. Sci. 103, 855-860.

Kramer N, Walzl A, Unger C, Rosner M, Krupitza G, Hengstschlager M, Dolznig H (2013) In vitro cell migration and invasion assays. Mutation Research 752, 10-24.

Krotscheck U, Boothe D M, Little A A, Erb H N. (2010) Pharmacokinetics of buprenorphine in a sodium carboxymethylcellulose gel after buccal transmucosal administration in dogs. Vet Ther. 11, E1-8.

Labelle M, Begum S. & Hynes R O (2011) Direct signalling between platelets and cancer cells induces epithelial-mesenchymal-like transitions and promotes metastasis Cancer Cell 20, 576-590.

Labelle M, & Hynes R O (2012). The initial hours of metastasis: the importance of cooperative host-tumor cell interactions during hematogenous dissemination. Cancer Discov. 12, 1091-9

Lal I, Dittus K, Holmes CE (2013) Platelets, coagulation and fibrinolysis in breast cancer progression. Breast Cancer Res. 15, 207.

Leader A, Zelikson-Saporta R, Rozovski U, Pereg D, Raanani P, Spectre G, Lishner M, Hermoni D (2015) Clopidogrel treatment is associated with a decrease in cancer incidence. ASH 57th Annual Meeting Orlando Fla. Dec. 5-8, 2015

Lee C H, Lin Y J, Lin C C, Yen C L, Shen C H, Chang C J, Hsieh S Y (2015). Pretreatment platelet count early predicts extrahepatic metastasis of human hepatoma. Liver Int. 35, 2327-36.

Lee M, Kim S W, Nam E J, Yim G W, Kim S, Kim Y T (2011) The impact of pretreatment thrombocytosis and persistent thrombocytosis after adjuvant chemotherapy in patients with advanced epithelial ovarian cancer. Gynecol Oncol. 122, 238-41.

Lee S Y, Kang T H, Knoff J, Hung C F, Wu T, Kang K O, Shim J J (2013) Depletion of platelets enhances therapeutic antitumour effects generated by therapeutic DNA vaccine. J. Immunotherapy of Cancer 1 (Suppl.1) 222.

Li F X, Wei L J, Zhang H, Li S X, Liu J T (2014) Significance of thrombocytosis in clinicopathologic characteristics and prognosis of gastric cancer. Asian Pac J Cancer Prev. 15, 6511-7.

Li F, Hu H, Gu S, Chen X, Sun Q. (2015) Platelet to lymphocyte ratio plays an important role in prostate cancer's diagnosis and prognosis Int J Clin Exp Med. 8, 11746-5.

Li R, Ren M, Chen N, Luo M, Deng X, Xia J, Yu G, Liu J, He B, Zhang X, Zhang Z, Zhang X, Ran B, Wu J. (2014) Presence of intratumoral platelets is associated with tumor vessel structure and metastasis. BMC Cancer. 14, 167, 1-10.

Li X, Koh A J, Wang Z, Soki F N, Park S I, Pienta K J, McCauley L K.(2011) Inhibitory effects of megakaryocytic cells in prostate cancer skeletal metastasis. J Bone Miner Res. 26,125-34.

Lin R J, Afshar-Kharghan & Schafer A I (2014) Paraneoplastic thrombocytosis: the secrets of tumor self-promotion. Blood 124, 184-187.

Lou X L, Sun J, Gong S Q, Yu X F, Gong R, Deng H. (2015) Interaction between circulating cancer cells and platelets: clinical implication. Chin J Cancer Res. 27,450-60.

Lv X, Li Y, Chen T, Li N (2010) Relationship between platelet count and gastric cancer stage and prognosis. Chinese-German J. of Clin. Onc. 9. 213-215.

Maeda H Brandon M Sano A (2003) Design of controlled release formulation for ivermectin using silicone (II) In. J. Pharm. 261, 9-19.

Maráz A1, Furák J, Varga Z, Kahan Z, Tiszlavicz L, Hideghety K (2013). Thrombocytosis has a negative prognostic value in lung cancer. Anticancer Res. 33(4):1725-9.

Martinez-Sellés M, Datino T, Figueiras-Graillet L, Gama J G, Jones C, Franklin R, and Fernández-Avilés F.(2013) Cardiovascular Safety of Anagrelide in Healthy Subjects: Effects of Caffeine and Food Intake on Pharmacokinetics and Adverse Reactions. Clin Drug Investig. 33, 45-54.

Mlot B & Rzepecki (2012) Cardiac complications of cancer treatment. Chapter 3 in "Cardiotoxicity on Oncologic Treatments" Edited by Fiuza M, InTech Europe. ISNB 978-953-51-0273-1.

Mishra A, Shiozawa Y, Pienta K J, Taichman R S. (2011) Homing of cancer cells to the bone. Cancer Microenviron. 4, 221-35.

Nieswandt B, Hafner M, Echtenacher B, Mannel D N. (1999) Lysis of tumor cells by natural killer cells in mice is impeded by platelets. Cancer Res. 59, 1295-300.

O'Keefe SC1, Marshall F F, Issa M M, Harmon M P, Petros J A (2002). Thrombocytosis is associated with a significant increase in the cancer specific death rate after radical nephrectomy. J Urol. 168(4 Pt 1):1378-80.

Paget S (1889) quoted in "The distribution of secondary growths in cancer of the breast". 1889. Cancer Metastasis Rev. 1989) 8, 98-101.

Pang Q, Zhang J Y, Xu X S, Song S D, Qu K, Chen W, Zhou Y Y, Miao R C, Liu S S, Dong Y F, Liu C (2015). Significance of platelet count and platelet-based models for hepatocellular carcinoma recurrence. World J Gastroenterol. 21 5607-21.

Park S I, Soki F N, McCauley L K. (2011) Roles of bone marrow cells in skeletal metastases: no longer bystanders. Cancer Microenviron. 4, 237-46.

Pathak Y & Thassu D (2009) Drug Delivery Nanoparticles Formulation and Characterization ISBN 9781420078046. Publishers Taylor & Francis Group.

Phutane P, Shidhaye S, Lotlikar V, Ghuule A, Sutar S and Kadam V (2010) In vitro evaluation of novel sustained release microspheres of glipizide prepared by emulsion-solvent diffusion evaporation method. J Young Pharm. 2, 35-42.

Psaila B (2010) Interactions between megakaryocytes and tumour cells in the bone marrow vascular stem cell niche promote tumour growth and metastasis. PhD Thesis, Imperial College London Rachidi S, Wallace K, Day T A, Alberg A J, Li Z. (2014) Lower circulating platelet counts and antiplatelet therapy independently predict better outcomes in patients with head and neck squamous cell carcinoma. J Hematol Oncol. 7, 65.

Rajkumar A, Szallasi A. (2013) Paraneoplastic thrombocytosis in breast cancer. Anticancer Res. 33 4545-6.

Rasheed A, Kumar K, Sravanthi V(2008) Cyclodextrins as drug carrier molecules: A review. Scienta Pharmaceutica 76, 567-598.

Reiss L (1872) Zur pathologischen Antomie des Blutes. Arch Anat. Physiol Wissensch Med. 39, 237-249.

Remington The Science and Practice of Pharmacy (2012-22nd edition) Edited by Allen, L V. Published by Pharmaceutical Press. ISBN 978 0 85711 062 6.

Riedl J, Pabinger I & Ay C(2014) Platelets in cancer and thrombosis Hamostaseologie. 2014/1, 1-9.

Saidi A & Alharethi R (2011) Management of chemotherapy induced cardiomyopathy Current Cardiology Review. 7, 245-249.

Sarfaraz Md, Venubabu P V, Doddayya H, Udupi R H (2011) Design and characterization of transmucosal drug delivery system of glibenclamide. Int. Research J. of Pharmacy. 2, 116-120.

Schumacher D, Strilic B, Sivaraj K K et al (2013) Platelet-derived nucleotides migration and metastasis via P2Y2 receptor. Cancer Cell 24, 130-137.

Shimada H, Oohira G, Okazumi S, Matsubara H, Nabeya Y, Hayashi H, Takeda A, Gunji Y, Ochiai T. (2004) Thrombocytosis associated with poor prognosis in patients with esophageal carcinoma J Am Coll Surg. 198 737-41.

Shire Pharmaceuticals (2013) Further information on the safety concern (of anagrelide) http://www.mhra.gov.uk/home/groups/comms-ic/documents/websiteresources/con228796.pdf Sierko E, Wojtukiewicz M Z (2004). Platelets and angiogenesis in malignancy. Semin Thromb Hemost. 30, 95-108.

Soares F A (1992) Increased numbers of pulmonary megakaryocytes in patients with arterial pulmonary embolism and with lung metastases seen at necropsy. J Clin Pathol 45, 140-2.

Stone R L, Nick A M, McNeish I A, Balkwill F, Han H D, Bottsford-Miller J, Rupairmoole R, Armaiz-Pena G N, Pecot C V, Coward J, Deavers M T, Vasquez H G, Urbauer D, Landen C N, Hu W, Gershenson H, Matsuo K, Shahzad M M, King E R, Tekedereli I, Ozpolat B, Ahn E H, Bond V K, Wang R, Drew A F, Gushiken F, Lamkin D, Collins K, DeGeest K, Lutgendorf S K, Chiu W, Lopez-Berestein G, Afshar-Kharghan V, Sood AK. (2012). Paraneoplastic thrombocytosis in ovarian cancer. N Engl J Med. 366, 610-18.

Stravodimou A, Voutsadakis I A, (2013). Pretreatment thrombocytosis as a prognostic factor in metastatic breast cancer. Internat. J. of Breast Canc. 2013, 1-6.

Sun C, Li Q, Hu Z, He J, Li C, Li G, Tao X, Yang A. (2013) Treatment and prognosis of anaplastic thyroid carcinoma: experience from a single institution in China. PLoS One. 8, 1-8.

Suzuki K, Aiura K, Kitagou M, Hoshimoto S, Takahashi S, Ueda M, Kitajima M. (2004) Platelets counts closely correlate with the disease-free survival interval of pancreatic cancer patients. Hepatogastroenterology. 51, 847-53.

Takagi S, Tsukamoto S, Kawano Y, Moschetta M, Mishima Y, Kokubun K, Manier S, Salem K, Huynh D, Sacco A, Roccaro A M, Johnson K E, Battinelli E M, Ghobrial I M (2015). Platelets/megakaryocytes are critical regulators of tumour progression in multiple myeloma. ASH 2015 Dec. 5-8, Orlando, Fla.

Verma G R, Thiagaraian S, Gupta R, KamanL, Das R, Kochhar R, Sinha S K (2015) J. Thrombocytosis and raised CRP levels predicts advanced esophageal carcinoma. Gastrointest. Cancer 46, 350-355.

Voglová J, Maisnar V, Beranek M, Chrobák L. (2006) Combination of imatinib and anagrelide in treatment of chronic myeloid leukemia in blastic phase. Vnitr Lek. 52, 819-22.

Voutsadakis I A (2014) Thrombocytosis as a prognostic marker in gastrointestinal cancers. World J of Gastrointest Oncol. 6, 34-40.

Wang G, Franklin R, Hong Y, Erusalimsky J D. (2005). Comparison of the biological activities of anagrelide and its major metabolites in haematopoietic cell cultures. Br. J. Pharmacol. 146, 324-32.

Wang H, Gao J, Bai M, Liu R, Li H, Deng T, Zhou L, Han R, Ge S, Huang D, Ba Y. (2014) The pretreatment platelet and plasma fibrinogen level correlate with tumor progression and metastasis in patients with pancreatic cancer. Platelets. 25, 382-7.

Wang L I, Huang X, Chen Y, Jin X, Li Q, Yi TN (2012). Prognostic value of TP/PD-ECGF and thrombocytosis in gastric carcinoma. Eur. J. Surg. Oncol. 38, 568-573.

Wang R T, Zhang L Q, Mu Y P, Li J B, Xu X S, Pang Q, Sun L K, Zhang X, Dong S B, Wang L, Liu C (2015). Prognostic significance of preoperative platelet count in patients with gallbladder cancer. World J Gastroenterol. 21, 5303-10.

Weilbacher K N, Guise T A and McCauley K (2011) Cancer to bone: fatal attraction. Nature Reviews Cancer 11, 411-25.

Williams M, Liu Z W, Woolf D, Hargreaves S, Michalarea V, Menashy R, Kooner I, Wilson E. (2012) Change in platelet levels during radiotherapy with concurrent and adjuvant temozolomide for the treatment of glioblastoma: a novel prognostic factor for survival. J Cancer Res. Clin Oncol. 138, 1683-8.

Wong R. S. M., Lam L. W. K., Cheng G. (2008) Successful rechallenge with anagrelide in a patient with anagrelide-associated cardiomyopathy. Ann Hematol. 87, 683-4.

Yeh E T, Yeh E T, Tong A T, Lenihan D J, Yusuf S W, Swafford J, Champion C, Durand J B, Gibbs H, Zafarmand A A, Ewer MS. (2004) Cardiovascular complications of cancer therapy toxicity. Circulation. 109, 3122-31.

Yuan L, Liu X. (2015) Platelets are associated with xenograft tumor growth and the clinical malignancy of ovarian cancer through an angiogenesis dependent mechanism Mol Med Reports 11, 2449-2458.

Yu D, Liu B, Zhang L, Du K.(2013) Platelet count predicts prognosis in operable non-small cell lung cancer. Exp Ther. Med. 5, 1351-1354.

Zhang W, Yu C, Huang B, Zhou F L, Huang H D, Li Q. (2015) Correlation between bone metastasis and thrombocytosis in pulmonary adenocarcinoma patients. Oncol Lett. 9, 762-768.

Zhang X, Ran Y.(2015) Prognostic role of elevated platelet count in patients with lung cancer: a systematic review and meta-analysis Int. J. Clin. Exp. Med, 8, 5379-87.

The invention claimed is:

1. A method of treating metastatic disease, comprising administering to a human thrombocytotic cancer patient in need thereof a therapeutic amount of a compound;
   wherein the human thrombocytotic cancer patient has a primary cancer;
   the site of the metastatic disease is a bone or lung of the human thrombocytotic cancer patient;
   the compound inhibits migratory attraction of circulating cancer cells towards megakaryocytes found at the bone or lung of the human thrombocytotic cancer patient; and
   the compound is anagrelide, or a pharmaceutically acceptable salt, solvate or active metabolite thereof, wherein the active metabolite of anagrelide is anagrelide that has been hydroxylated at position 5, 8 or 9, oxidized at the tertiary nitrogen position forming an N-oxide, or a combination thereof.

2. The method of claim 1, wherein the compound is formulated as a formulation selected from the group consisting of sublingual tablets, buccal spray, mucoadhesive buccal tablets, mucoadhesive buccal films, buccal lozenges, buccal lollipops, rectal suppositories, rectal gels, nasal spray, pulmonary delivery devices, transdermal patches, transdermal gels, transdermal ointment, transdermal creams, and injectable formulations.

3. The method of claim 1, wherein the human thrombocytotic patient has a platelet count that is reduced to an upper limit of 400×103/μL but above a lower limit of 150×103/μL.

4. The method of claim 1, wherein the human thrombocytotic patient has a platelet count that is reduced to an upper limit of 350×103/μL but above a lower limit of 150×103/μL.

5. The method of claim 1, wherein the human thrombocytotic patient has a platelet count that is reduced to an upper limit of 300×103/μL, but above a lower limit of 150×103/μL.

6. The method of claim 1, wherein the human thrombocytotic patient has a platelet count that is reduced to an upper limit of 250×103/μL, but above a lower limit of 150×103/μL.

7. The method of claim 2, wherein the formulation is an injectable formulation; and the is formulated for intravenous, intramuscular, or subcutaneous administration.

8. The method of claim 1, wherein the primary cancer is a cancer of the brain, a cancer of the oral cavity, a cancer of the head and neck, thyroid carcinoma, gastrointestinal cancers, pancreatic cancer, hepatocellular cancer, colorectal cancer, cancer of the lungs, cancer of the ovaries, a cancer of the endometrium, a cancer of the cervix, breast cancer, prostate cancer, a cancer of the kidneys, skin mesothelioma, melanoma, a cancer of the gallbladder, or multiple myeloma.

9. The method of claim 1, wherein the primary cancer is a cancer of the lungs, a cancer of the ovaries, a cancer of the kidneys, or a colorectal cancer.

10. The method of claim 1, wherein the primary cancer is a cancer of the lungs.

11. The method of claim 1, wherein the primary cancer is a cancer of the ovaries.

12. The method of claim 1, wherein the primary cancer is a cancer of the kidneys.

13. The method of claim 1, wherein the primary cancer is a colorectal cancer.

\* \* \* \* \*